US007148028B2

(12) United States Patent
Petyaev

(10) Patent No.: US 7,148,028 B2
(45) Date of Patent: Dec. 12, 2006

(54) METHODS AND MEANS RELATING TO ATHEROSCLEROSIS

(75) Inventor: Ivan Petyaev, Cambridge (GB)

(73) Assignee: Cambridge Theranostics Ltd., Cambridge (GB)

( * ) Notice: Subject to any disclaimer, the term of this patent is extended or adjusted under 35 U.S.C. 154(b) by 105 days.

(21) Appl. No.: 10/225,461

(22) Filed: Aug. 22, 2002

(65) Prior Publication Data

US 2003/0194746 A1 Oct. 16, 2003

Related U.S. Application Data

(60) Provisional application No. 60/355,655, filed on Feb. 6, 2002, provisional application No. 60/323,127, filed on Sep. 18, 2001.

(30) Foreign Application Priority Data

| | | |
|---|---|---|
| Aug. 22, 2001 | (GB) | 0120428.8 |
| Feb. 18, 2002 | (GB) | 0216755.9 |
| Feb. 27, 2002 | (GB) | 0204611.8 |
| Jul. 16, 2002 | (GB) | 0216530.6 |

(51) Int. Cl.

| | |
|---|---|
| ***G01N 33/573*** | (2006.01) |
| ***C07K 16/00*** | (2006.01) |
| ***C12N 9/00*** | (2006.01) |
| ***C12P 21/08*** | (2006.01) |

(52) U.S. Cl. .......................... 435/7.4; 435/7.1; 435/7.2; 435/7.32; 435/188.5; 436/518; 436/519

(58) Field of Classification Search ................. 435/7.1, 435/7.2, 7.32, 7.36, 7.91, 28, 29, 188.5, 7.4; 436/518, 519

See application file for complete search history.

(56) References Cited

U.S. PATENT DOCUMENTS

| | | |
|---|---|---|
| 5,278,189 A | 1/1994 | Rath et al. |
| 6,281,199 B1 | 8/2001 | Gupta |

FOREIGN PATENT DOCUMENTS

| | | |
|---|---|---|
| EP | 0561744 A1 | 9/1993 |
| EP | 0669132 A1 | 8/1995 |
| WO | 92/05780 A1 | 4/1992 |
| WO | 97/41227 | 11/1997 |
| WO | 98/57622 A1 | 12/1998 |
| WO | 01/22958 A2 | 4/2001 |

OTHER PUBLICATIONS

Saikku et al, Annals of Internal Medicine, 116(4):273-278, 1992).*

Shoenfeld et al (Trends in Immunology, 22(6):293-295, Jun. 2001).*

Kelley et al, (Environmental Health Perspectives, 106(7):375-384, Jul. 1998).*

ICN product catalog 92/93.*

Roitt et al., Immunology, Third Edition, Mosby 1993. pp. 4.1-4.3).*

Schwenke et al, Vitamin E. Combined With Selenium Inhibits Atherosclerosis in Hypercholesterolemic Rabbits Independently of Effects on Plasma Cholesterol Concentrations, Circ. Res., Aug. 24, 1998, vol. 83, pp. 366-377.

Fong et al, Can an Antibiotic (Macrolide) Prevent *Chlamydia pneumoniae*-Induced Atherosclerosis in a Rabbit Model? Clinical and Diagnostic Laboratory Immunology, Nov. 1999, vol. 6, No. 6, pp. 891-894.

Muhlestein et al, Infection With *Chlamydia pneumonaie* Accelerates the Development of Atherosclerosis and Treatment With Azithromycin Prevents It in a Rabbit Model, Circulation, vol. 97, pp. 633-636.

Petyaev, Extraction of anti-lipoprotein abzymes from human atherosclerotic lesion: antibodies which bind and oxidise LDL, J Submicroscop Cytol Pathol; vol. 32, pp. 477 (2000).

Kalayoglu et al, Cellular Oxidation of Low-Density Lipoprotein by *Chlamydia pneumoniae*, J Infect Disease, 1999, vol. 180, pp. 780-790.

Burian et al, Independent and Joint Effects of Antibodies to Human Heat-Shock Protein 60 and *Chlamydia pneumoniae* infection in the Development of Coronary Atherosclerosis, Circulation, 2001, vol. 103, pp. 1503-1508.

Petyaev et al, Superoxide Dismutase Activity of Antibodies Purified from the Human Arteries and Athersclerotic Lesions, Biochemical Society Transactions, Feb. 1998, vol. 26, No. 1, p. S43.

Sobal et al, Influence of Acetylsalicylic Acid on Oxidation of Native and Glycated Low-Density Lipoprotein, Life Sciences, Apr. 7, 2000, vol. 66, No. 20, pp. 1987-1998.

Steer et al, Aspirin protects low density lipoprotein from oxidative modification, Heart, 1997, vol. 77 No. 4, pp. 333-337.

Gurfinkel et al, Emerging role of antibiotics in atherosclerosis, American Heart Journal, Nov. 1999, vol. 138, No. 5, pp. S537-538.

Imanishi et al, Jpn Circ. J., 2001, vol. 65, No. 6, pp. 556-560.

Kolodgie et al, Cardiovascular Disease, Feb. 2001, vol. 19, No. 1, pp. 127-139.

Rodriguez-Malaver et al, FEBS Letters, 1997, vol. 406, pp. 37-41.

Turley et al, Free Radical Biology & Medicine, 2000, vol. 29, No. 11, pp. 1129-1134.

Wilkins et al, Biochimica et Biophysica Acta, 1994, vol. 1215, pp. 250-258.

Lamb et al, FEBS Letters, 1994, vol. 352, pp. 15-18.

* cited by examiner

*Primary Examiner*—Patricia A. Duffy
(74) *Attorney, Agent, or Firm*—Nixon & Vanderhye P.C.

(57) ABSTRACT

The present invention relates to the identification of lipid oxidising antibodies as a key pathogenic factor in atherosclerotic disorders. The presence of such antibodies is a important marker for the diagnosis and prognosis of such disorders and methods and means for the assessment of athersclerotic conditions are provided herein.

21 Claims, 7 Drawing Sheets

Interaction of ovine Chlamydia with anti-ApoB antibodies

Absorption at 340nm vs. Ovine Chlamydia, in $10^6$ cells/ml

○ Chlamydia + Anti-ApoB antibodies
□ [Anti-ApoB antibodies + ApoB] + Chlamydia

METHODS AND MEANS RELATING TO ATHEROSCLEROSIS

This application claims the benefit of Provisional Application No. 60/323,127, filed 18 Sep. 2001 and 60/355,655, 06 Feb. 2002, the entire content of which is hereby incorporated by reference in this application.

FIELD OF INVENTION

The present invention relates to methods for assessing and treating atherosclerosis and related conditions in an individual. Methods of the present invention are useful in the clinical diagnosis, prognosis, prophylaxis and therapy of atherosclerosis and related disorders.

BACKGROUND OF INVENTION

Auto-antibodies against such lipids as cholesterol [Swartz G. M., Jr., et al Proc. Natl. Acad. Sci. USA (1988), 85, 1902–1906, Alving C. R. and Swartz G. M., Jr. Critical Reviews in Immunology (1991), 10, 441–453.], phospholipids [Alving C. R. Biochem. Soc. Trans. (1984), 12, 342–344.] and low density lipoproteins (LDL) are found in human plasma [Kabakov A. E. et al Clin. Immun. Immunopath. (1992), 63, 214–220, Mironova M et al Ibid. (1997), 85, 73–82.] and are involved in the development of atherosclerosis [Lopes-Virella M. F. and Virella G. Clin. Immun. Immunopath. (1994), 73, 155–167, Kiener P. A. et al Arterioscler. Thromb Vasc. Biol. (1995), 15, 990–999.].

Separately, neither antibodies nor LDL are a pathogenic factor, only the immune complex of the two [Tertov V. V et al Atherosclerosis (1990), 81, 183–189, Orekhov A. N. et al Biochem. Biophys. Res. Comm. (1989), 162, 206–211.].

Immune complexes comprising unmodified plasma lipoproteins are known to have a low atherogenicity. However, if the lipoproteins become modified, in particular oxidised, these immune complexes become highly atherogenic [Orekhov A. N. et al Biobhem. Biophys. Res. Comm. (1989), 162, 206–211, Orekhov A. N. et al Arterioscler. Thromb. Vasc. Biol. (1991), 11, 316–326.] Oxidation of plasma lipids, which takes the form of peroxidation, is generally considered to be responsible for the development of atherosclerosis and is a consistently observed and published feature of this disease in the clinic [Goto Y. In: Lipid Peroxides in Biology and Medicine, Ed. Yagi K., Academic Press, New York, London, Tokyo (1982), 295–303, Halliwell D. and J. M. C. Gutteridge, Free Radicals in Biology and Medicine, Clarendon Press, Oxford, 1989, Schultz D et al Arterioscler. Thromb. Vasc. Biol. (2000), 20, 1412–1413]. However, until the present disclosure, the cause of this peroxidation in plasma was obscure.

SUMMARY OF THE INVENTION

The present invention relates to the discovery that a particular sub-group of auto-antibodies are capable of both binding and oxidising lipids and lipoproteins. These catalytic antibodies react with and oxidise low density lipoprotein to generate atherogenic factors and are the first reported example of anti-lipid abzymes.

Various aspects of the present invention provide methods for assessing an individual for an atherosclerotic disorder.

A method for assessing an individual for an atherosclerotic disorder method may comprise:

testing the ability of an antibody from a sample obtained from the individual to oxidise lipid.

DETAILED DESCRIPTION OF INVENTION

Figure 1:
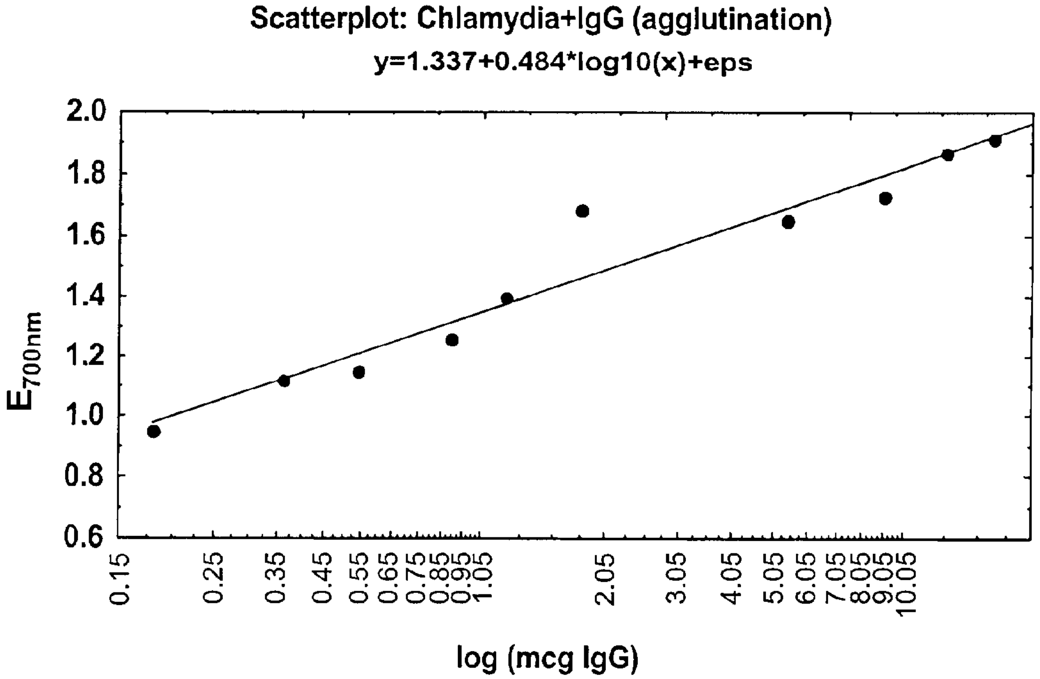
FIG. 1 shows the results of an agglutination reaction between 100 µl of ovine *Chlamydia* and IgG extracted from human atherosclerotic lesion.

Catalytic antibodies as described herein have been found to have various applications relating to atherosclerotic disorders, for example in methods for assessing, determining or detecting an atherosclerotic disorder in an individual. Such methods may be used to determine the presence or severity of an atherosclerotic disorder in an individual or to determine the risk that an individual will in the future suffer from an atherosclerotic disorder.

The presence in the sample of an antibody which oxidises lipid is indicative of the individual having or suffering from an atherosclerotic disorder or being at risk of suffering from such a disorder in the future. The amount, level or activity of such antibodies is indicative of the severity of the disorder i.e. increased amounts and/or activity of antibody are indicative of increase severity of disorder. These methods are therefore suitable for determining the presence and/or severity of an atherosclerotic disorder in an individual.

Such a method may, for example, comprise capturing an antibody from a serum sample, for example using an immobilised anti-idiotypic antibody, and determining the lipid oxidation activity of the captured antibody.

A lipid oxidising antibody is a molecule which is a member of the immunoglobulin super-family (e.g. an immunoglobulin such as IgG, IgM or IgE) which is associated with both binding and catalytic activity. After purification, for example, using protein G, a lipid oxidising antibody displays both binding to antigen and catalytic activity (i.e. lipid oxidation).

Both binding and catalytic activities may be intrinsic to a lipid oxidising antibody. Alternatively, the lipid oxidising activity may be due to a catalytic molecule which is tightly bound to the antibody and co-purifies with it (for example, using a Protein G/Protein A or Protein L column) in a complex. This catalytic molecule may be an immunoglobulin or a non-immunoglobulin, such as an enzyme or a metal ion. After purification, the complex displays binding activity from the antibody and catalytic activity from the catalytic molecule. A lipid oxidising antibody may, alternatively, initiate lipid oxidation by another mechanism e.g. by altering the lipid antigen environment (e.g. via the activation of monocytes) or altering the lipid or lipoprotein to facilitate oxidation of lipid.

A catalytic antibody may be specific for a particular epitope which is carried by a number of antigens and may therefore bind to different antigens which carrying the same epitope. The antibody may show no significant binding to other epitopes. The antibody is thus said to 'bind specifically' to the epitope or to an antigen comprising the epitope. An epitope which is recognised by the antibody may be shared by a host molecule and an antigen from an infectious agent, for example a bacterium, fungus, virus or protozoa. A lipid oxidising antibody produced by a host in response to a foreign antigen, for example during pathogenic infection, may thus cross-react with host lipids or lipoproteins or other antigens.

The lipid oxidising antibody may thus bind to both a host molecule and a foreign antigen and may catalyse the oxidation of one or both of these molecules.

An antigen be a member of a family of molecules sharing high sequence identity (i.e. homologues) which are found in a range of infectious agents (for example, in two or more species of gram—ve bacteria) or the antigen may be specific to a particular infectious agent (i.e. it does not have homologues in other species). Moreover, the same epitope may be present in antigens from different infectious agents which do not otherwise share high levels of sequence identity (i.e. non-homologues). Examples of antigens which are common to a range of infectious agents include apo-lipoprotein B, OmpA, lipopolysaccaride (LPS), hsp60 MQMP, (P)OMP, p54 and lipid A.

Individuals which may be the subject of methods of the present invention include humans and non-human animals, including domestic animals such as dogs, cats, horses and parrots, farm animals such as sheep and cattle and rare or exotic animals such as elephants and tigers. References to 'human' herein should be understood to include 'non-human animal' except where the specific context dictates otherwise.

An antibody in a method as described herein may be isolated, purified and/or extracted from a sample, or it may be comprised within a serum, plasma, blood or other biological sample obtained from an individual. Preferably the antibody is in a blood, serum or plasma sample and may, for example be an IgG molecule.

Antibody molecules which catalyse the oxidation of lipid are referred to herein as catalytic antibody molecules, anti-lipid abzymes, abzymes or lipid oxidising antibodies. As described above, such catalytic antibodies may have an intrinsic or inherent lipid oxidase activity or other activity which leads to lipid oxidation or may be naturally associated (i.e. bound or attached in a non-covalent manner in their natural state within the body) with a molecule having lipid oxidase activity.

Methods as described herein may be useful in determining whether an individual has an atherosclerotic condition and determining the appropriate course of treatment. For example, a method may comprise testing the ability of an antibody from a sample obtained from an individual to oxidise lipid, and; reducing antibody-mediated lipid oxidising activity in the vascular system of the individual, if necessary as described below.

The experimental data in the present application further shows that a sub-group of the antibodies which are raised in response to *Chlamydia* infection are auto-antibodies which cross react with host antigen and are responsible for plasma lipid peroxidation. Catalytic anti-*Chlamydia* antibodies are shown to be present in anti-lipoprotein IgG fractions extracted from human atherosclerotic lesions and the sera of patients with clinical complications of atherosclerosis, but absent from IgG extracted from the sera of healthy people. Catalytic antibodies which bind and oxidise lipid as described herein may therefore be reactive with i.e. bind to, a *Chlamydia* cell.

Whilst atherosclerosis has been linked in the past to the presence in the arterial wall of the bacteria *Chlamydia pneumoniae* [Roivainen M. et al Circulation (2000), 101, 252–257, Siscovick D. S. et al. J. Infect. Dis. (2000), 181, Suppl. 3, S417–420 and U.S. Pat. No. 6,281,199], a serological test to detect specific anti-*Chlamydia* antibodies in the plasma or serum of patients [Mendall M. et al (1995) J. Infect. 30 121–128, Wang S -P et al (1970) 70 367–374] cannot be used to identify or distinguish a patient with atherosclerosis. A significant part of the population have a history of *Chlamydia* infection and, as result of this, have specific anti-*Chlamydia* antibodies in their sera, without any clinical manifestation of atherosclerosis [Davidson M. et al Circulation (1998), 98, 628–633 m, Song Y. G. et al Yonsei Med. J.(2000), 41, 319–327.]. The presence of anti-*Chlamydia* antibodies per se in the plasma or serum is not therefore indicative of atherosclerosis.

However, catalytic anti-*Chlamydia* antibodies which cross-react with human antigens and catalyse the oxidation of plasma lipoproteins are shown herein to be useful both as markers for atherosclerotic disorders and targets for the treatment of such disorders.

An assay method for assessing an individual for an atherosclerotic disorder may thus comprise:

testing the ability of an antibody from a sample obtained from an individual to bind to a *Chlamydia* cell antigen and to oxidise lipid.

In some embodiments, a method may include:

determining the lipid oxidation activity of an antibody molecule from a sample obtained from the individual, wherein said antibody molecule binds to a *Chlamydia* antigen.

In other embodiments, a method may include:

determining the binding to a *Chlamydia* antigen of an antibody molecule from a sample obtained from the individual, wherein said antibody molecule possesses lipid oxidation activity (i.e. oxidises lipids).

In still further embodiments, a method may include:

determining the binding to a *Chlamydia* antigen of an antibody molecule from a sample obtained from an individual; and, determining the lipid oxidation activity of said antibody molecule.

The presence in a sample of an antibody molecule which is reactive with (i.e. binds) a *Chlamydia* antigen and which possesses the biological activity of oxidising lipid, is indicative of the individual either suffering from or being susceptible to or at risk of an atherosclerotic disorder. i.e. a method may further comprise inferring from said activity and binding whether said individual has an atherosclerotic disorder.

The amount or level of lipid oxidising antibody present in the sample is indicative of the severity of the condition. Such an antibody molecule may oxidise, in particular peroxidise, the lipid portion of plasma lipoproteins, in particular low density lipoproteins, for example Apo-B, as described below.

Lipid oxidising antibody molecules may be anti-*Chlamydia* abzymes or antibody molecules i.e. they bind or are reactive with a *Chlamydia* cell antigen.

A *Chlamydia* antigen as described herein may be any immunogen or immunogenic component of a *Chlamydia* cell i.e. a molecule from *Chlamydia* which evokes or is capable of evoking an immune response in a mammal against the *Chlamydia* cell, for example Hsp60 (Huittinen et al (2001) Eur Resp. J. 17(6) 1078–1082, Kinnunen A. et al (2001) Scand. J. Immunol. 54(1–2) 76–81). Preferably, the antigen is a protein or lipid antigen i.e. it comprises or consists of a lipid group or moiety. A lipid antigen may be, for example, a lipid, lipoprotein or other lipid associated cell component which binds anti-*Chlamydia* antibodies and the term 'lipid antigen' refers to any of these components. An example of a suitable lipid antigen is lipopolysaccaride (LPS) An antigen may be purified and/or isolated, or comprised within a *Chlamydia* cell, preferably on the surface of a *Chlamydia* cell. Suitable methods for purifying and/or isolating such a lipoprotein are well known in the art, for example HPLC.

Antibodies raised against human apo-lipoprotein B have been shown to be reactive with *Chlamydial* cells (see Example 7).

In some embodiments, a lipid oxidising antibody as described herein may thus be reactive with human apolipoprotein B. Such an antibody may also be reactive with *Chlamydia* lipopolysaccaride (LPS).

A Chlamydial cell may be a cell from a species belonging to the *Chlamydia psittaci* group. The *Chlamydia psittaci* group includes *Chlamydia psittaci* and *Chlamydia pneumoniae*. In some preferred embodiments, the Chlamydial cell is an ovine *Chlamydia psittaci* cell. Suitable preparations of live ovine *Chlamydia psittaci* in a lyophilised form are available commercially (Intervet).

As described above, lipid oxidation, such as peroxidation, is one of the main processes leading to the conversion of circulating lipoproteins into highly atherogenic factors [Goto Y. (1982) supra, Halliwell B., and J. M. C. Gutteridge, (1989) supra, Schultz D., and Harrison D. G. (2000) supra] and catalytic antibodies, for example catalytic antibodies raised in response to Chlamydial infection, represent a key pathogenic factor which is responsible for the development of atherosclerosis. Furthermore, this role makes these catalytic antibodies an important target for therapeutic intervention in atherosclerosis-related conditions.

Methods of assessing an atherosclerotic disorder as described herein, are useful in determining the optimal therapeutic treatment for an individual. For example, an individual having anti-lipid abzymes indicative of an atherosclerotic condition may be subjected to therapeutic treatment to alleviate the condition or its symptoms. The level or amount of anti-lipid abzymes is indicative of the severity of the condition and may be used to determine whether or not a particular therapeutic course is appropriate.

An individual who is found to be susceptible to or at an increased risk of suffering from an atherosclerotic disorder may undergo treatment, for example, with antioxidants or antibiotics as described below, to reduce the risk that the disorder will occur, to delay or prevent the onset or reduce the severity of the disorder.

The present invention thus encompasses methods which further comprise the step of reducing the antibody-mediated lipid oxidation activity in said individual, in particular in the vascular system of said individual, as described below.

Figure 2:
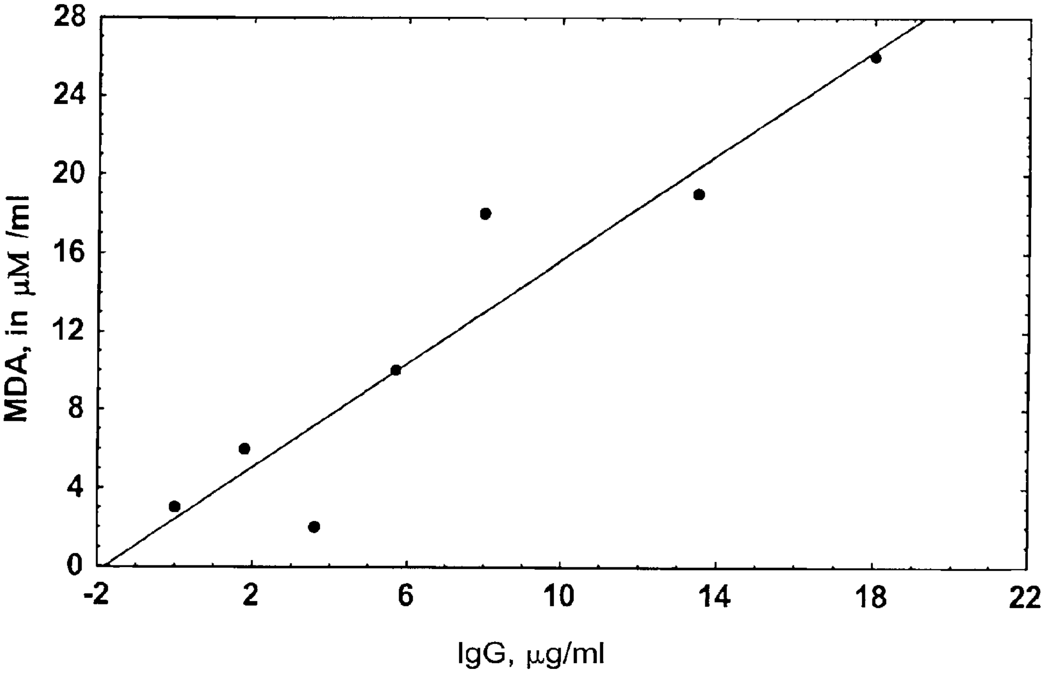
FIG. 2 shows the dependence of ovine *Chlamydia* peroxidation on the concentration of human atherosclerotic lesion IgG. Concentration of *Chlamydia* was constant and the pH was 5.7.

Whilst current serological tests for anti-*Chlamydia* antibodies are designed to measure their level in dilutions or titers and are semi-quantitative, methods described herein allow the measurement of the degree of lipid peroxidation caused by the catalytic fraction of these antibodies. The degree of the development of the oxidation reaction is a linear function of the concentration of catalytic anti-*Chlamydia* antibodies present in the sample (see FIG. 2). The present methods therefore provide a quantitative assay which provides for the measurement of the level of catalytic anti-*Chlamydia* antibodies in the sample.

Methods for assessing an atherosclerotic condition as described herein may include quantifying, measuring or determining the amount of antibody molecule in a sample. The amount can be determined by any convenient method, for example by determining the amount, level or degree of lipid oxidation or lipid oxidation activity and correlating this with the amount of antibody molecule present.

Quantification of the amount of catalytic anti-*Chlamydia* antibody in a sample from an individual may be used to quantify the degree of risk or susceptibility of the individual to an atherosclerotic disorder.

Furthermore, the amount of catalytic anti-*Chlamydia* antibody in a sample may also be indicative of the severity of the disorder. Methods described herein are therefore useful in the diagnosis and prognosis of an atherosclerotic condition in an individual.

Lipid oxidation activity, including lipid peroxidation activity, may be determined by determining (for example by measuring or detecting) the oxidation of host lipid (i.e. lipid from the sample), lipid from a foreign antigen such as a *Chlamydia* cell, or lipid from another source, which may for example be added as part of an assay method.

Lipid oxidation may be determined by measuring the accumulation of products or by-products, such as co-oxidised coupled reporter molecules or the disappearance or consumption of substrates such as non-modified lipids or co-substrates such as oxygen.

Many methods for determining lipid peroxidation are known in the art and are suitable for use in accordance with the present invention. The precise mode of determining lipid oxidation is not a feature of the present invention and those skilled in the art are able to choose a suitable mode according to their preference and general knowledge.

Suitable methods are, for example, described in CRC Handbook of Methods for Oxygen Radical Research, CRC Press, Boca Raton, Fla. (1985), Oxygen Radicals in Biological Systems. Methods in Enzymology, v. 186, Academic Press, London (1990); Oxygen Radicals in Biological Systems. Methods in Enzymology, v. 234, Academic Press, San Diego, New York, Boston, London (1994); and Free Radicals. A practical approach. IRL Press, Oxford, New York, Tokyo (1996)

In preferred embodiments, oxidation is determined by determining the production (i.e. the presence or amount) of a lipid oxidation product.

Oxidation products and/or intermediates of the lipids in which oxidation was initiated may be determined or oxidation products and/or intermediates may be determined of lipids in which oxidation is propagated.

A suitable lipid oxidation product may include aldehydes such as malondialdehyde (MDA), (lipid) peroxides, diene conjugates or hydrocarbon gases. Lipid oxidation products may be determined by any suitable method. For example, lipid peroxidation products may be determined using HPLC (Brown, R. K., and Kelly, F. J In: Free Radicals. A practical approach. IRL Press, Oxford, New York, Tokyo (1996), 119–131), UV spectroscopy (Kinter, M. Quantitative analysis of 4-hydroxy-2-nonenal. Ibid.,133–145), or gas chromatography-mass spectrometry (Morrow, J. D., and Roberts, L. J. $F_2$-Isoprostanes: prostaglandin-like products of lipid peroxidation. Ibid., 147–157).

The peroxidation of lipid may lead to an oxidation of proteins, carbohydrates, nucleic acids and other types of molecules. The products of such oxidation can also be used for indirect measurement of the activity of the abzymes. In addition, peroxidation may lead to changes in the properties of reporter molecules associated with propagating lipid oxidation. As described below, reporter molecules may be encapsulated in these lipids, for example as liposomes, and release of the reporter molecule from the liposome is indicative of oxidation.

Suitable reporter substances and molecules may include intact luminous bacteria, luminol, lucigenin, pholasin and luciferin. Such substances may, for example, be coupled to $H_2O_2/O_2.^-/O_2$-utilizing molecules such as peroxidase, esterase, oxidase, luciferase, catalase, superoxide dismutase, perylene, $NAD^+$, and acridinium esters bis (trichlorophenyl) oxalate (Campbell A. K. Chemiluminescence. VCH, Ellis Horwood Ltd., England, 1988)

Other materials susceptible to free radical chain reactions may also be used to determine lipid oxidation. For example, lipid peroxidation, as a chain process, initiates and enhances the polymerisation of acrylamide. Lipid oxidation may thus be determined by the determining the co-polymerisation of $^{14}C$-acrylamide (Kozlov Yu P. (1968) Role of Free Radicals in normal and pathological processes. Doctorate thesis—MGU Moscow 1968)

Since lipid and lipoprotein peroxidation is a free radical mediated process, lipid oxidising abzymes may be measured by detection of these radicals. Radicals may be detected or determined using intrinsic low-level chemiluminescence (with or without sensitisors) (Vladimirov, Y. A., and Archakov, A. I. Lipid Peroxidation in Biological Membranes. Nauka, Moscow (1972); Vladimirov, Y. A. Intrinsic low-level chemiluminescence. In: Free Radicals. A practical approach. IRL Press, Oxford, New York, Tokyo (1996), 65–82)., electron spin resonance (with spin trapping (Mason, R. P. In vitro and in vivo detection of free radical metabolites with electron spin resonance. In: Free Radicals. A practical approach. IRL Press, Oxford, New York, Tokyo (1996), 11–24) or without spin trapping (Petyaev, M. M. Biophysical approaches in the diagnosis of cancer. Medicina, Moscow (1972)) or other techniques well known in the art. Lipid oxidation may also be determined by determining the consumption of fatty acids or other substrates of this reaction.

In some preferred embodiments, the production of malondialdehyde (MDA) is determined, following reaction with 2-thiobarbituric acid (conventiently 1 mM) by measuring absorbance at an appropriate wavelength such as 525 nm.

Lipid which is oxidised by an anti-*Chlamydia* abzyme may include the lipid moiety of a lipoprotein, fatty acid, phospholipid, cholesterol, cholesterol ester or triglyceride. As described above, the lipid oxidation activity of an abzyme may also lead to the oxidization of protein, carbohydrate and/or nucleic acid, for example the protein and/or carbohydrate moieties of a lipoprotein.

Chlamydial lipid oxidation is determined in some preferred embodiments because it provides for a convenient one step assay, which may be used to determine, for example, the presence or absence of an anti-*Chlamydia* abzyme. Oxidation of Chlamydial lipid will occur when a *Chlamydia*-specific antibody is present which binds and oxidises Chlamydial antigen comprising a lipid.

In methods according to these preferred embodiments, an antigen may be a Chlamydial cell antigen.

For example, a method for assessing an atherosclerotic condition in an individual may include;

i) contacting a sample provided by an individual with a Chlamydial cell antigen; and ii) determining the oxidation of lipid in said sample.

Determining the oxidation of the lipid may include determining, for example measuring or detecting, the amount, level or degree of oxidation which is induced as a result of contact with the *Chlamydia* antigen. Preferably, the Chlamydial cell antigen is a lipid antigen and the oxidation of the Chlamydial cell lipid antigen is determined.

An antigen may be purified and/or isolated or, more preferably, it may be comprised within an intact cell membrane. In preferred embodiments, the antigen may be comprised with (e.g. on the surface of) a *Chlamydia* cell For example, a preferred method for assessing an atherosclerotic condition in an individual may comprise;

i) contacting a sample provided by an individual with a *Chlamydia* cell; and ii) determining the oxidation of the lipid of said cell.

The oxidation of lipid, for example in a sample, in the presence of the *Chlamydia* cell or antigen may be compared with the oxidation of lipid in the absence of the *Chlamydia* cell or antigen. An increase in lipid oxidation is indicative of the presence of an anti-lipid abzyme.

Lipid/lipoprotein peroxidation is a free radical chain reaction and is capable of self-propagation from one molecule to another, to a lipid-contained micelle, or to a whole cell (after attaching to its membrane via receptors or non-specific absorption) (Chemical and Biochemical Aspects of Superoxide and Superoxide Dismutase. Elsevier/North-Holland, New York, Amsterdam (1980); Lipid Peroxides in Biology and Medicine. Academic Press, Orlando, San Diego, San Francisco, New York, London (1982); Halliwell, B., and Gutteridge, J. M. C. Free Radicals in Biology and Medicine. Clarendon Press. Oxford (1996); Oxidants, Antioxidants, and Free Radicals. Taylor and Francis, Washington (1997)).

In some embodiments of the methods described herein, the propagation of peroxidation is used to facilitate the detection of lipid-oxidising abzymes.

For example, a microcontainer such as a liposome, vesicle or microcapsule which has a membrane which made of a material susceptible to free radical decomposition, for example a phospholipid membrane, may be loaded with a dye, fluorochrome or other reporter substance or detecting material, for example: Eosin, Fluorescamine, Rhodamine B or Malachite Green, and used in the detection of a lipid oxidising abzyme Lipid oxidation in the methods described herein may thus be determined by determining the release of the encapsulated reporter substance.

The loaded microcontainer may be mixed with a sample of plasma or serum. A *Chlamydia* antigen, conveniently comprised in or part of a *Chlamydia* cell, is then added to the mixture. Any lipid oxidising abzymes in the sample then bind to the antigen are initiate peroxidation.

Initiation of the lipid/lipoprotein oxidation by the interaction of *Chlamydia* antigen with an abzyme will self propagate and spread to the coating of the microcontainer. This damages the coating and causes the release of the reporter substance into the surrounding solution. This release is then detected.

A method may include;

i) contacting a sample provided by an individual with a Chlamydial cell antigen in the presence of a microcontainer susceptible to lipid oxidation and containing a reporter substance; and ii) determining the release of said reporter substance from the microcontainer.

Reporter substance release occurs as a result of contacting said antibody with the microcontainer containing the reporter substance or a composition comprising the microcontainer containing the reporter substance.

If the intensity of the signal produced by the release of the reporter is not sufficient to cause a registerable or detectable signal, a free radical propagator or sensitiser can be included in the reaction mixture, for example; free ions and complexes of $Fe^{2+}/Co^{2+}$ or other metals of transient valence These and other sensitisers serve to multiply the amount of free radicals in a system.

Release of incorporated material from the microcontainer leads to changes in the physical/chemical properties of the reaction mixture which can be registered visually (or by other conventional means). Alternatively, damaged/fragmented/dissolved microcontainers can be separated from unmodified ones either by active centrifugation or by passive sedimentation.

Instead of liposomes or other microcontainers (loaded with reporter substances), erythrocytes from the blood sample itself may be used as a target for the propagating lipid/lipoprotein peroxidation caused by anti-lipid abzymes.

*Chlamydia* bacteria or antigens may be introduced or contacted with a blood sample, optionally in the presence of a sensitiser to ensure propagation of the peroxidation reaction. Lipid oxidation may be determined by determining the haemolysis of erythrocytes in the blood sample.

Any initiation of the lipid/lipoprotein oxidation by the interaction of *Chlamydia* antigen with abzyme in the sample will self propagate and spread to the erythrocyte cell membrane, leading to damage and eventually cell lysis. The appearance of haemolysis in the sample of the whole blood in response to the addition of *Chlamydia* bacteria/antigens is therefore indicative of the presence of lipid oxidising abzymes. Haemolysis may be determined by any suitable method.

A method may include;

i) contacting a sample provided by an individual and comprising erythrocytes with a Chlamydial cell antigen; and ii) determining the haemolysis of said erythrocytes.

Haemolysis occurs as a result of contacting said antibody with the erythrocytes or a composition comprising the erythrocytes.

These embodiments may be preferred in some circumstances because samples do not require a separation of plasma/serum from the erythrocytes prior to their analysis. Liposomes or other microcontainers may be loaded with, for example, a material which can develop a colour different to the red colour of haemoglobin. Alternatively, spinning of the tested samples or even passive sedimentation would separate undamaged microcontainers/erythrocyte. Release of reporter dye or haemolysis is indicative of the presence of lipid-oxidising antibodies in the analysed material. The intensity of the signal correlates with their activity/concentration.

Since whole blood may be analysed using the methods described above, no centrifugation step is required and these methods may be used in non-laboratory or domestic conditions. The presence or severity of atherosclerosis may, for example, be determined by comparing the observed reporter signal or haemolysis with known values in atherosclerosis patients and normal individuals. Such a comparison may be carried out using a chart, scale, graph or calibration which indicates the amount or level of reporter signal or haemolysis at particular stages or severities of atherosclerosis.

Lipid peroxidation is a redox process which may also be measured using a coupled redox system. Suitable redox systems include physical and chemical systems. For example a sensor chip may be used to detect changes in the redox potential of a lipid oxidation reaction coupled thereto. A range of sensor chips based either on redox enzymes or on redox mediators are known in the art. Both of these types of sensors can be adjusted/used for the detection of free radical molecules or redox molecules coupled with them (Hall E. A. H. Biosensors. Redwood Press Ltd., Great Britain, 1990).

Accumulation of $H_2O_2$ produced by lipid peroxidation may be measured, for example, by addition of the coupled peroxidase-based reaction which will use hydrogen peroxide to oxidise its other co-substrate(s) and produce a coloured product. An accumulation of $O_2.^-$ produced by lipid peroxidation can be determined by using $O_2.^-$ sensitive molecules, such as cytochrome C or riboflavin.

Alternatively, lipid peroxidation consumes molecular oxygen, hence any $O_2$-dependent chemical reaction or physical process can be used, for example, oxygen electrode or polarography. (Polarography, Ed. Kolthoff I. M., Lingane J. J. Interscience Publishers, New York, London, 19520

Methods according to some aspects of the present invention may include obtaining a sample of blood, serum or plasma from an individual. A test sample of serum or plasma may be obtained, for example, by extracting blood an individual and isolating the serum or plasma from the extracted blood. Suitable extraction methods include centrifugation to separate serum and plasma from cellular material.

In using assay methods of the present invention, the skilled person is well aware of the need to employ appropriate control experiments.

An atherosclerotic disorder or condition as described herein may include atherosclerosis, ischaemic (coronary) heart disease, myocardial ischaemia (angina), myocardial infarction, aneurismal disease, atheromatous peripheral vascular disease, aortoiliac disease, chronic and critical lower limb ischaemia, visceral ischaemia, renal artery disease, cerebrovascular disease, stroke, atherosclerotic retinopathy, thrombosis and aberrant blood clotting, and hypertension. Such conditions may be medical or veterinary conditions.

The conditions described above are closely related and a predisposition to one such condition may be indicative of a predisposition to other such conditions.

Methods as described above may be used to determine or assess the presence and/or severity of an atherosclerotic disorder in an individual. Further, such methods may be used to determine whether an individual who has no symptoms of atherosclerosis may be susceptible to atherosclerosis in the future An individual who is susceptible to such a disorder may have a predisposition to that disorder which places that individual at a higher risk of incurring the disorder during their lifetime than the population as a whole. Although at a higher risk of doing so, a susceptible individual may, in fact, never incur the disorder.

Abzymes, in particular anti-*Chlamydia* abzymes, may preferentially bind to and oxidise certain isoforms of lipoprotein within a population, such as apolipoprotein E $\epsilon 4$.

An aspect of the present Invention provides a method of determining the susceptibility of an individual to atherosclerosis comprising;

in a sample obtained from an individual which comprises a lipoprotein which has two or more isoforms within a population, determining the presence in said sample obtained from the individual of a lipoprotein isoform which binds to an lipid oxidising antibody preferentially, relative to said other isoforms.

Individuals who have a lipoprotein isoform which binds preferentially to, or is preferentially oxidised by, a lipid oxidising antibody as described herein relative to other isoforms of the lipoprotein within the population have an increased susceptibility to an atherosclerotic condition relative to other members of the population.

Examples of lipoprotein isoforms associated with a disease condition may include apolipoprotein E $\epsilon 4$.

As described above, in an individual identified as suffering from or being susceptible to an atherosclerotic disorder using a method as described herein, may comprise the further step of reducing or lowering antibody-mediated lipid oxidation activity of said individual, in particular in the vascular system of the individual. The may be achieved for example, by administering an antioxidant and/or an antibiotic to said individual.

Methods as described herein may be also used to predict or detect the incidence of atherosclerotic disorders in a population and estimate the severity of such disorders.

Such a method may comprise;

testing the ability of antibody from one or more samples obtained from a population to oxidise lipid.

In preferred embodiments, the ability of an antibody to bind to a foreign antigen, for example an antigen from a pathogen such as *Chlamydia*, may be tested.

The proportion of samples taken from a population which contain an anti-lipid abzyme, for example a catalytic anti-*Chlamydia* antibody, may be used to determine the incidence and/or severity of atherosclerotic disorders within the population.

Other aspects of the present invention provide the use of one or more foreign (i.e. non human) antigens which elicit lipid oxidising antibodies in a method of assessing an individual for an atherosclerotic disorder, in particular the use of an isolated *Chlamydia* cell or isolated *Chlamydia* antigen in a such a method. Suitable *Chlamydia* antigens may include Hsp60, OmpA, ApoB and lipopolysaccaride (Kalayoglu M. et al (2000) J. Infect. Dis. 181 Suppl 3: S483–9). Reagents for use in a method as described herein, such as isolated *Chlamydia* cells or antigens, may be provided as part of a kit, e g. in a suitable container such as a vial in which the contents are protected from the external environment. Cells may be provided in a lyophilised form. The kit may include instructions for use of the cells, e.g. in a method for determining the presence or absence of anti-*chlamydia* abzymes in a sample. A kit may include one or more other reagents required for the method, such as sample and cell diluents, exogenous lipid or lipoprotein, and/or reagents for determining lipid oxidation, such as sensitisers and reporters. A kit for use in determining the presence or absence of anti-*Chlamydia* abzymes and therefore the presence and the severity of atherosclerosis in an individual to a condition as described herein may include one or more articles and/or reagents for performance of the method, such as means for providing the test sample itself, e.g. a syringe for removing a blood sample (such components generally being sterile) and vessels such as tubes or curvettes for carrying out the test.

Another aspect of the present invention provides a kit comprising an isolated *Chlamydia* cell and an oxidation determining reagent or an isolated *Chlamydia* antigen and an lipid oxidation determining reagent for use in a method of determining an atherosclerotic disorder in an individual.

A kit may further comprise instructions for assessing an individual for an atherosclerotic disorder and/or buffers or reagents for assessing an individual for an atherosclerotic disorder.

Lipid oxidation determining reagents may include a denaturant. In addition to denaturing lipids and proteins in the assay, a denaturant may stop biochemical reactions, extract MDA from accompanying molecules and provide an optimum pH for detection of the extracted MDA. Suitable denaturants include trichloroacetic acid, $H_2SO_4$ and phosphotungstic acid.

Trichloroacetic acid may be used at 5% to 75% concentration, more preferably 25% to 55% for example, 30% ,40% or 50%. $H_2SO_4$ may be used at 0.5 to 10 M, more preferably 2 M to 5 M for example 3 M or 4 M $H_2SO_4$. Phosphotungstic acid may be used at 1% to 30%, more preferably 5% to 15%, for example 10% (w/v) phosphotungstic acid.

Lipid oxidation determining reagents may also include a detection reagent which reacts with an oxidised lipid product such as MDA to produce a signal. A suitable detection reagent is 2-thiobarbituric acid (TBA), which may conveniently be 1 mM. This reacts with MDA to produce a colour change detectable at 525 nm. This lipid oxidation can be determined by determining the change in absorbance at 525 nm.

Other suitable detection reagents include n-butanol, which is suitable for use in fluorescent assays, for example involving the measurement of the inherent fluorescence of MDA [Brown, R. K., and Kelly, F. J. Peroxide and other products. In: Free Radicals. A practical approach. IRL Press, Oxford, New York, Tokyo (1996), 119–131

Antigen may be provided in a crude form (i.e. suspension of a whole cells) in isolated or purified form, synthetic or recombinant form, or in the form of epitope-imitating anti-idiotypic antibodies or their fragments.

An example of a kit according to this aspect of the present invention comprises live ovine *Chlamydia* (lyophilised form), PBS (to dissolve bacteria), 0.05M acetate buffer pH 4.0, 40% trichloroacetic acid and 1 mM 2-thiobarbituric acid.

A kit for use in performing a method according to another aspect of the present invention may include;

i) a microcontainer ii) a reporter substance iii) a *Chlamydia* antigen

A microcontainer may be a liposome, vesicle or microcapsule which comprises a membrane which is degraded or damaged by oxidation so as to render it permeable i.e. allow release of its contents. Such a membrane is susceptible to the propagation of abzyme catalysed peroxidation from *Chlamydia* bacteria or antigens.

The reporter substance may be a dye, fluorochrome or other detection material or label, as described above. The reporter substance in the kit may be encapsulated within the microcontainer, or it may be supplied as a separate reagent which is then encapsulated in the microcontainer by the user prior to use.

A *Chlamydia* antigen is an antigen which elicits an immune response in Chlamydial infection, in particular an antigen which elicits auto-catalytic antibodies. The antigen may be comprised in a complex or a *Chlamydia* cell. Suitable antigens may include the *Chlamydia* Hsp60 and ApoB antigens.

A kit may further comprise instructions for assessing an individual for an atherosclerotic disorder and/or buffers or reagents for assessing an individual for an atherosclerotic disorder.

A kit according to another aspect of the present invention may include;

i) sensitiser which allows or facilitates the propagation of lipid peroxidation ii) *Chlamydia* antigen Sensitiser is a substance or agent which propagates the lipid peroxidation reaction from the *Chlamydia* antigen to other reactive species, such as a red blood cell (erythrocyte) membrane.

A kit may further comprise instructions for assessing an individual for an atherosclerotic disorder and/or buffers or reagents for assessing an individual for an atherosclerotic disorder.

Kits of the present invention may additionally comprise two vessels, e.g. tubes, curvettes, bottles, wells or jars. One such vessel may be used for the control sample of blood (i.e. a control vessel) and one may be used for the addition of *Chlamydia* antigen (i.e. test vessel). Such vessels may be coated with an anti-coagulent. Suitable anti-coagulents are well known in the art.

Where the vessels are not coated with anti-coagulent, the kit may separately comprise an anti-coagulent.

As described above, a kit may also comprise instructions for use according to a method described herein. A kit may further comprise a chart, scale, graph or curve which calibrates the intensity of the signal produced by the kit (i.e. haemolysis or release of reporter substance) with the severity of the atherosclerosis or other atherosclerotic disorder in a patient. This allows both the presence of an atherosclerotic disorder and its severity to be determined from the sample. The chart and/or instructions may be in paper form or may be in the form of a computer program product stored on a data recording means, which may be a computer hard drive or a CD-ROM or floppy disk.

Aspects of the present invention will now be illustrated with reference to the accompanying figures described above and tables and experimental exemplification below, by way of example and not limitation. Further aspects and embodiments will be apparent to those of ordinary skill in the art.

All documents mentioned in this specification are hereby incorporated herein by reference.

Table 1 contains data showing the effect of the IgG fraction extracted from human atherosclerotic lesion on lipid peroxidation of *Chlamydia* bacteria; pH 5.7; all measurements made in triplicate.

Table 2 contains data showing the cross-reactivity for lesion IgG between human serum lipoproteins and ovine strain of *Chlamydia psittaci;*

Table 3 contains data showing the effect of feline *Chlamydia* on lipid peroxidation in human serum; all measurements made in triplicate.

Table 4 contains data showing the role of IgG in the initiation of lipid peroxidation by ovine *Chlamydia* in human plasma, all measurements made in triplicate.

Table 5 contains data showing the effect of the addition of ovine *Chlamydia* into the control sera and in the sera of patients with clinical complications of atherosclerosis.

Table 6 shows the inhibition of lipid oxidizing activity of atherosclerotic lesion IgG by antioxidant inhibitors.

Table 7 shows examples of metal chelators which may be used in accordance with the present invention.

Table 8 shows examples of anti-microbials which may be used in accordance with the present invention.

Table 9 shows examples of anti-oxidants which may be used in accordance with the present invention.

Table 10 shows levels of lipid oxidising anti-*Chlamydia* antibodies in healthy and infected sheep (figures in brackets represent % increase/decrease against control).

Table 11 shows the inhibition of abymes using metal chelators.

Table 12 shows the inhibition of in vitro abzyme activity using metal chelators.

Table 13 shows the effect of aspirin on the activity of anti-*Chlamydia* abzymes in patients with Coronary Heart Disease.

Table 14 shows the effect of aspirin on the activity of anti-*Chlamydia* abzymes in patients with Silent Myocardial Ischaemia.

Table 15 shows abzyme activity in patients treated with anti-microbial agent.

Table 16 shows abzyme activity in patients treated with an antimicrobial agent plus aspirin daily.

Table 17, shows the clinical condition of patients treated with anti-microbial agent only.

Table 18 shows average abzyme levels in groups of individuals suffering from atherosclerosis related conditions.

Table 19 shows individual abzyme levels in patients suffering from angina, who were either receiving or not receiving aspirin.

Table 20 shows the induction of abzymes in rabbits inoculated with *Chlamydia.*

Table 21 shows the effect of formalin treated *Chlamydia* in rabbits having induced abzymes.

Table 22 shows anti-*Chlamydia* abzyme activity in patients treated by azithromycin, 500 mg daily (therapy group A)

Table 23 shows anti-*Chlamydia* abzyme activity in patients treated by azithromycin, 500 mg, plus aspirin, 250 mg, daily (therapy group B).

Table 24 shows anti-*Chlamydia* abzyme activity in patients treated by azithromycin, 500 mg daily plus antioxidants (therapy group C).

Table 25 shows anti-*Chlamydia* abzyme activity in therapy group D patients treated by aspirin, 250 mg daily (therapy group D).

Table 26 shows anti-*Chlamydia* abzyme activity in the patient control group.

Table 27 shows a summary of the results of anti-abzyme therapy.

Table 28 shows an evaluation of the severity of angina pectoris by modified Rose-Blackburn Questionnaire before and after treatment.

Table 29 shows abzyme and Rose-Blackburn Test scores before and after treatment for THD patients who tested negative for anti-*Chlamydia* IgG.

Table 30 shows the inhibitory properties of azithromycin on abzymes.

Table 31 shows the effect of various drugs on anti-*Chlamydia* abzyme activity.

Table 32 shows the effect of anti-abzyme therapy on clotting times and thrombosis.

EXPERIMENTS

Materials and Methods

Samples 3 samples of sera were used from 22 patients with clinical complications of atherosclerosis admitted for coronary artery and abdominal aorta by-pass operations in the Cardio-Vascular Surgery Centre of the Clinical Hospital No.1 in Rostov-na-Donu, Russia. 20 of these patients were male and 2 female, aged between 47 and 66. One of these patients, No.6/6a had an acute myocardial infarction at the moment of the testing, hence in some final calculations the data from this patient were not included. The control group was comprised of clinically healthy volunteers 5 of whom were male and 5 female aged between 40 and 55.

Pieces of atheromas from abdominal aorta from 7 of these patients were used to extract IgG fraction by a protein A sorbent as described below.

Extraction of IgG from Atherosclerotic Lesion

The pieces of aorta (approximately 200–400 mg wet weight) were cut into pieces of approximately 10 mg each, placed in 5.0 ml of PBS with 1% non-ionic detergent Igepal CA-630 and homogenised by a mechanical homogeniser (Ultra-Turrax) at full-power with a 15 mm probe three times for 3 seconds each with 20 second cooling intervals. After homogenisation the insoluble components were separated by centrifugation at 5000 g for 10 minutes and supernatants were used for analysis.

The supernatant was treated with protein A attached to cross-linked 4% beaded agarose at 37° C. for 30 minutes. The immunoglobulin fraction attached to the beads was then spun down at 5000 g for 10 minutes and the supernatant decanted. In order to remove any lipoproteins attached to the sedimented immunoglobulins, the samples were re-suspended with 10% of Igepal CA-630. They were then centrifuged at 5000 g for 10 minutes and the supernatant was decanted.

To remove the detergent three subsequent washings were performed in the excess of the phosphate buffer with centrifugation under the same regime. The removal of lipoprotein from the immunoglobulin fraction was confirmed by the absence of cholesterol in this fraction.

Determination of anti-*Chlamydia* Abs

Blood was collected from an ante-cubital vein in the morning after an overnight fast, serum was separated and frozen at −20° C. prior to being tested.

The presence of anti-*Chlamydia* antibodies was measured in the agglutination reaction with ovine *Chlamydia* cells and by ELISA (recombinant antigen-based) assays.

For the agglutination reaction, gradual dilutions of the tested sera were incubated for 24 hours at 37° C. with $10^6$ of live ovine *Chlamydia*. The appearance of aggregates was detected and estimated at 700 nm. The ELISA assay was performed in accordance with manufacturer's instructions (Medac).

A titre$\geqq$1.64 was considered to be seropositive.

Determination of Peroxidation of Lipids

Lipid peroxidation was assessed as a level of MDA concentration which was measured by spectrophotometric method (Draper, H. H. et al Free Radic. Biol. Med. (1993) 15, 353]. This method is based on the formation of a coloured product when malondialdehyde reacts with thiobarbituric acid.

Cross Reactivity between Serum Lipoproteins and *Chlamydia*

The IgG fraction comprising anti-*Chlamydia* abzymes was extracted from a human atherosclerotic lesion as described above. 100 µl of this fraction (containing 1 µg/ml) was pre-incubated with 890 µl of whole or delipidated serum from a healthy donor for 1 hour at 37° C.; pH 5.7.

Lipoproteins (and associated material) were removed from the serum by preparative ultra-centrifugation in KBr solution in accordance with the earlier described method [Havel R. J et al. J. Clin. Invest. (1955) 34, 1345–1353. 22].

$10^5$ *Chlamydia psittaci* cells (Intervet) in a 10 µl volume were then added to the serum. The amount of oxidation induce by contact with the *Chlamydia* cells was then determined using the method described above.

In the presence of binding between the anti-*Chlamydia* abzymes and the plasma lipoproteins, no additional oxidation on contact with the *Chlamydia* cells is observed, because the anti-*Chlamydia* abzymes are removed by the ultracentrifugation.

In the absence of binding between the anti-*Chlamydia* abzymes and the plasma lipoproteins, oxidation is observed on contact of the plasma with the *Chlamydia* cells, because the anti-*Chlamydia* abzymes are still be present in the sample.

Assay for Anti-*Chlamydia* Abzymes

Reagents used in assaying anti-*Chlamydia* abzymes are as follows;

1. Live ovine *Chlamydia* (lyophilised form)
2. PBS (to dissolve bacteria)
3. 0.5M acetate buffer pH 4.0
4. 40% trichloroacetic acid
5. 1 mM 2-thiobarbituric acid.

The presence or amount of catalytic anti-*Chlamydia* antibodies in a sample was detected as follows;

1. Samples of tested sera are diluted 1:1 by 0.05M acetate buffer pH 4.0 to make the final pH of these samples between 5.6–5.8.
2. 990 µl of the diluted serum mixed with 10 µl of the commercial live ovine *Chlamydia* vaccine.
3. samples are then incubated overnight (12–16 hours) at 37° C.
4. To each sample 250 µl of 40% trichloroacetic acid and 250 µl of 1 mM 2-thiobarbituric acid are added.
5. All samples are placed in a water bath and boiled for 30 minutes.
6. Samples are cooled down and centrifuged at 3,000 g for 10 minutes.

7. Supernatants are collected and their absorption is measured at λ 525 nm to determine the concentration of malondialdehydes (MDA) which are products of lipid peroxidation.

Results

EXAMPLE 1

IgG was extracted from an atherosclerotic lesion in a patient using the method described above. Anti-*Chlamydia* antibodies were found to be present in this IgG fraction (FIG. 1).

Figure 3:
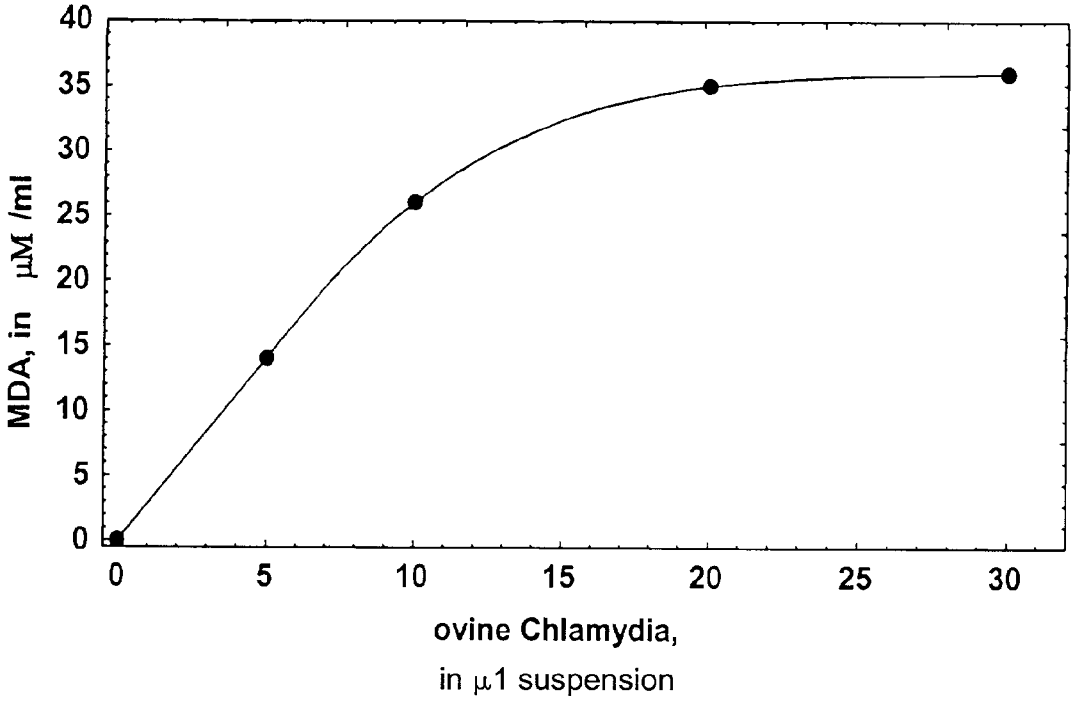
FIG. 3 shows the Michaelis-Menten kinetics of lipid peroxidation in ovine *Chlamydia* by 1.8 µg human atherosclerotic lesion IgG; apparent $K_M$=13.3–16 1µl of *Chlamydia* suspension; pH 5.7.

The ability of the extracted IgG fraction to oxidize lipid was determined. The IgG fraction was shown to cause a peroxidation of lipids in both ovine and feline strains of *Chlamydia psittaci* (table 1). Kinetic analysis of this peroxidation reaction showed that the reaction had an enzymatic character (FIGS. 2, 3) *Chlamydia* bacterium can therefore be considered as a substrate for their antibodies extracted from human atherosclerotic lesion.

The epitopes for anti-*Chlamyidia* abzymes were investigated further using non-ionic detergents. Treatment of *Chlamydia* with Triton X-100 or Igepal CA-630 abolished the oxidation of the lipids in the bacteria by the extracted abzymes. Similar results were obtained for the treatment of human serum low density lipoproteins.

This provides indication that either the epitopes for the catalytic antibodies are conformational and/or the integrity of the antigen is important to initiate the oxidation of lipids in both lipoproteins and *Chlamydia.*

The ability of anti-*Chlamydia* abzymes to cross-react with plasma lipoproteins was then determined. IgG extracted from atherosclerotic lesion was pre-incubated with serum from a patient to allow anti-lipoprotein antibodies in the extract to interact with non-modified lipoproteins. The lipoproteins and antibodies bound thereto were then removed by ultra-centrifugation.

Catalytic anti-*Chlamydia* antibodies were found to be removed with the lipoprotein (Table 2). This demonstrates that the catalytic anti-*Chlamydia* antibodies cross-react with both serum lipoproteins and the ovine strain of *Chlamydia* bacteria.

The presence of anti-*Chlamydia* antibodies in the serum of atherosclerosis patients was then investigated. The addition of ovine *Chlamydia* to the serum of the patients was observed to cause an increase in lipid peroxidation within the sample. A similar effect was observed with a feline *Chlamydia* strain (table 3).

The observed effects were due to presence of lipid oxidising anti-*Chlamydia* antibodies in the fraction of IgG in patient sera (table 4) Catalytic antibodies from the serum of atherosclerosis patients were therefore observed to cross-react with both lipoproteins and ovine *Chlamydia*

Correlative analysis of the concentration of anti-*Chlamydia* and anti-lipoprotein antibodies in human sera showed that both these parameters have a statistically significant positive link with the high correlation coefficient 0.82. This provides further indication that the same antibody possesses both binding activities.

Figure 4:
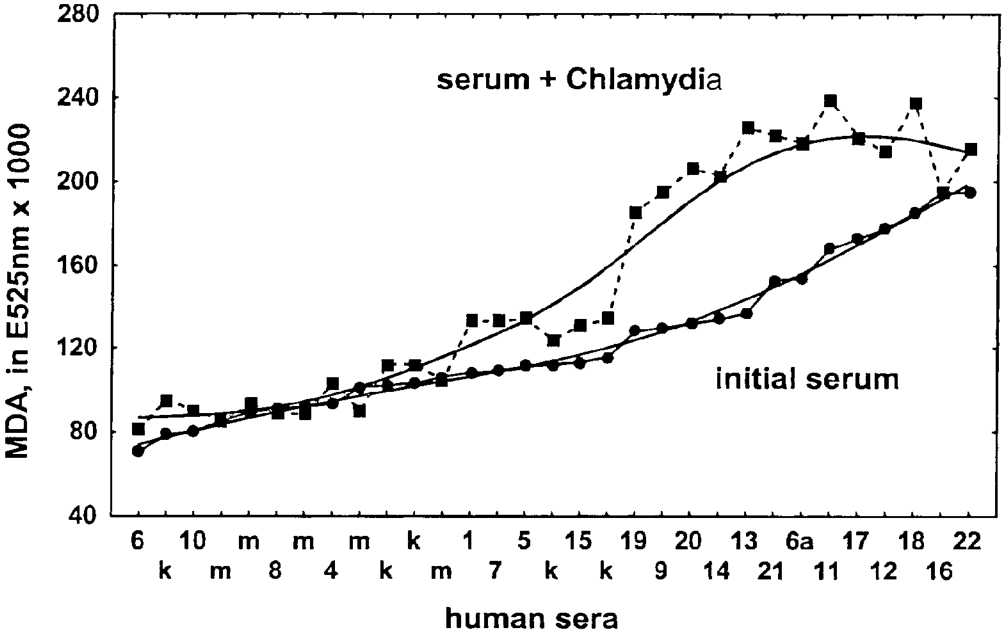
FIG. 4 shows the effect of the addition of ovine *Chlamydia* suspension on lipid peroxidation in human serum. 10 µl of the bacterial suspension was added to 990 µl of the diluted 1:1 serum; pH 5.7; all the mixed samples were incubated at 37° C. for 18 hours (numbers of sera are the same as in table 5).

In studies, with atherosclerosis patients using the assay method described above, catalytic anti-*Chlamydia* antibodies were found in 81% of the patients with clinical complications of atherosclerosis and only in 10% of the control group (FIG. 4, table 5). This demonstrates that these antibodies are a pathogenic marker of this disease.

This study demonstrates for the first time the existence of anti-lipids/lipoproteins abzymes in biological systems. Their occurrence in atherosclerosis but not in healthy individuals indicates that these abzymes play an important role in the pathogenesis of this disease and its complications. It can also interlink such main biochemical/immunological disorders as the activation of lipid peroxidation, the occurrence of anti-lipoprotein antibodies and *Chlamydia* infection, all of which are involved in the development of atherosclerosis.

The presence of lipid-oxidising anti-*Chlamydia* antibodies in the plasma of an individual indicates that the pathological changes specific for this disease have already started. Since these abzymes are responsible for a lipid/lipoprotein oxidation and this process usually correlates with the degree/intensity of generalisation of atherosclerosis, the level/activity of anti-lipid-abzymes reflects the severity of this disease.

Changes in the lipoprotein profile and the elevation of the total cholesterol in plasma/serum are the only specific risk factors established for atherosclerosis. However, these changes can be detected for only 10–15% of all patients with clinical complications of this disease. Detection of lipid-oxidising anti-*Chlamydia* antibodies is the second specific marker for atherosclerosis, but has a much higher diagnostic value than the measurement of the lipid parameters described above.

The methods herein are therefore widely applicable in the diagnosis and prophylaxis of atherosclerosis and related conditions.

EXAMPLE 2

Inhibition of Lipid Peroxidation

Human Specimens

Antibodies were extracted from advanced atherosclerotic lesions of human aorta retrieved from four male patients, age range 53–64, during bypass surgery of an abdominal aortal stenosis at the Centre of Cardio-Vascular Surgery of Clinical Hospital No.1 in Rostov-na-Donu, Russia. After recovery these samples were immediately put in 30% w/v solution of NaCl and stored at 0–4° C. for 1–2 weeks prior to examination.

In control experiments, it was shown that during this period the activities of such enzymes as trypsin, catalase, superoxide dismutase, glutathione peroxidase, creatine kinase and lactate dehydrogenase, together with a level of immunoglobulin (IgG) fragmentation and the degree of lipid peroxidation (concentration of malonaldehydes) did not significantly change.

The pieces of aorta (approximately 200–400 mg wet weight) were cut into pieces of approximately 10 mg each, placed in 5.0 ml of PBS with 1% non-ionic detergent Igepal CA-630 and homogenised by a mechanical homogeniser (Ultra-Turrax) at full-power with a 15 mm probe three times for 3 seconds each with 20 second cooling intervals. After homogenisation the insoluble components were separated by centrifugation at 5000 g for 10 minutes and supernatants were used for analysis.

Antibody Extraction

The antibodies were extracted and analysed separately from the lesions of the four pieces of the abdominal aorta obtained from the four different patients.

The first step was the treatment of the supernatant with protein A attached to cross-linked 4% beaded agarose at 37° C. for 30 minutes After that the immunoglobulin fraction attached to the beads was spun down at 5000 g for 10 minutes. The supernatant was decanted. In order to remove any lipoproteins attached to the sedimented immunoglobulins, the samples were re-suspended with 10% of Igepal CA-630. They were then centrifuged at 5000 g for 10 minutes and the supernatant was decanted. To remove the detergent three subsequent washings were performed in the excess of the phosphate buffer with centrifugation under the same regime. The removal of lipoprotein from the immunoglobulin fraction was confirmed by the absence of cholesterol in this fraction.

Lipoproteins

Low density lipoproteins, d=1.030–1.050, were obtained from the plasma of healthy donors by sequential preparative ultracentrifugation in KBr solution in accordance with the earlier described method [Havel R. J. et al J. Clin. Invest. (1955) 34, 1345–1353]. LDL can be already associated with plasma immunoglobulins in these preparations [Bauer B. J. et al Atherosclerosis (1982), 44, 153–160].

These immunoglobulins can potentially either interfere with a reaction between LDL and their antibodies attached to the protein A, or can be bound by the latter protein itself. To avoid these possible artefacts, it was important, before the titration of lipoproteins with lesion antibodies in the affinity tests, to remove LDL with antibody attached using a saturated amount of protein A agarose beads.

In order to determine the level of LDL (in terms of cholesterol concentration), the calibration curve was made for every new batch of lipoproteins and during every new experiment LDL Peroxidation by Lesion IgG Samples of LDL with or without (control) tested antioxidants were incubated with lesion IgG for 16 hours at 37° C. at pH 5.6. The level of lipid peroxidation, in terms of the concentration of malondialdehyde (MDA), was measured by the following procedure. To 1.0 ml of each sample were added 250 μl of 40% trichloroacetic acid and 250 μl of 1 mM 2-thiobarbituric acid. After boiling the samples in a water bath for 30 minutes, they were cooled down and centrifuged at 3,000 g for 10 minutes. Supernatants were collected and their absorption measured at λ 525 nm.

The results of this experiment are presented in Table 6.

A range of inhibitors with antioxidant activity were observed to reduce the lipid oxidation activity of antibodies isolated from atherosclerotic plaques below the limit for detection in this assay. All these compounds therefore inhibit the activity of lipid oxidizing antibody.

Isolated abzymes were assayed in vitro for catalytic activity as described herein in the presence various antioxidant inhibitors of the following classes:

Iron (Fe2+) chelators—tetracycline

Copper (Cu2+) chelators—DDC, aspirin and penicillamine

General metal chelators—CN—, N3, DTPA (chelates free ions only) and picolinic acid.

Results are shown in Table 11.

These results show that abzyme inhibition occurs through copper chelation rather than iron chelation. Three separate copper chelators were demonstrated to block activity and these results suggest that the abzymes contact a bound copper ion as catalytic centre.

EXAMPLE 3

Clinical Example of Reduction in Lipid Oxidising Anti-*Chlamydia* Antibody Activity Patient—A. M. P., Caucasian, male, 43 years old, having clinical symptoms resembling the early stages of angina pectoris with complaints of transient unprovoked chest pain in combination with breathlessness. However, an ECG revealed no pathological changes in the heart.

The results of a blood test on Dec. 27, 2000 revealed normal total cholesterol and LDL-cholesterol levels; titers of anti-*Chlamydia* IgG and IgA antibodies were both 1:64 (ELISA, Medac). However, lipid-oxidising anti-*Chlamydia* abzymes were detected and their activity was 32 μM MDA (mean figure of triplicate measurement) per 1 ml of his serum.

The following daily treatment, over the course of three months, was recommended: Tetracycline hydrochloride 500 mg in combination with an antioxidant cocktail—Vitamin E 20 mg, Vitamin A 1.5 mg, Vitamin B6 3.2 mg, Ascorbic acid 180 mg, Zinc Gluconate 30 mg, L-Selenomethionine 100 μg per.

In three months after the beginning of the therapy complaints of chest pain and breathlessness disappeared. At the end of March, at the end of the treatment and almost exactly 3 months after treatment started, the analysis of his serum showed no changes in anti-*Chlamydia* IgG and IgA antibody titers (1:64 (ELISA, Medac)) At the same time the presence of anti-*Chlamydia* abzymes was not detectable.

Two weeks later the test was repeated with the same result.

EXAMPLE 4

The Influence of Ovine *Chlamydia* on Lipid Peroxidation of Ovine Sera

Sheep were vaccinated with Chlamydial cells using standard techniques and tested for abzyme activity. The results are set out in Table 10.

Pre-vaccinated sheep were disease-free and healthy and showed no significant changes between assay levels with and without *Chlamydia.*

Post-vaccination, sheep showed very high levels of anti-*chlamydia* antibodies but insignificant/no levels of abzymes.

Post abortion (wild type) represents sheep with chlamydiosis disease which have aborted due to the occlusion of the vascular system in the uterus in these, the level of abzyme activity verified by the addition of *Chlamydia* is significantly higher than without *Chlamydia.*

These results show that adminstration of Chlamydial vaccine may reduce or prevent the production of lipid oxidising antibodies.

EXAMPLE 5

The Association of Abzyme Activity and Arterial Stenosis

The activity of lipid-oxidising anti-*Chlamydia* antibodies and the degree of arterial stenosis in two different clinical groups was investigated. The first was a group of patients with Ischaemic Heart Disease (IHD) and the second a group of patients with Ischaemic Cerebrovascular Disease (ICD).

Coronary Artery Stenosis

Figure 5:
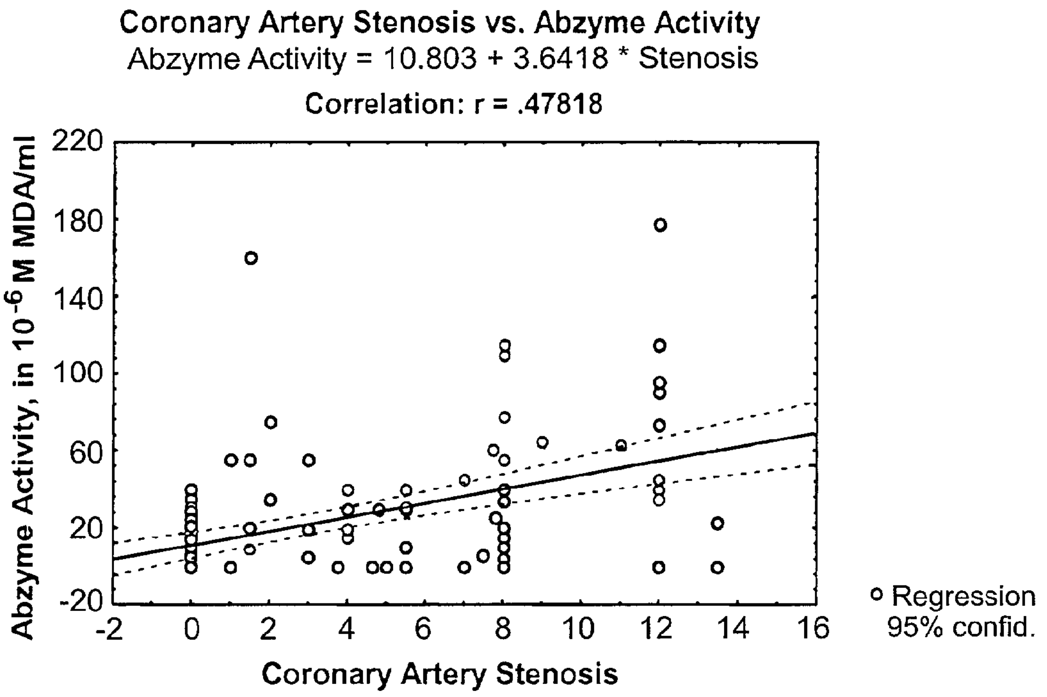
FIG. 5 shows the correlation between the degree of coronary artery stenosis and the activity of lipid-oxidising anti-*Chlamydia* antibodies in IHD patients. Severity of the stenosis is presented in terms of a score, which was calculated as an integral parameter of the stenosis of coronary arteries estimated by angiography.

The preliminary results of the trial show a positive and significant correlation between the activity of the anti-*Chlamydia* abzymes and the severity of the stenosis of coronary arteries of patients with IHD (FIG. 5).

Figure 6:
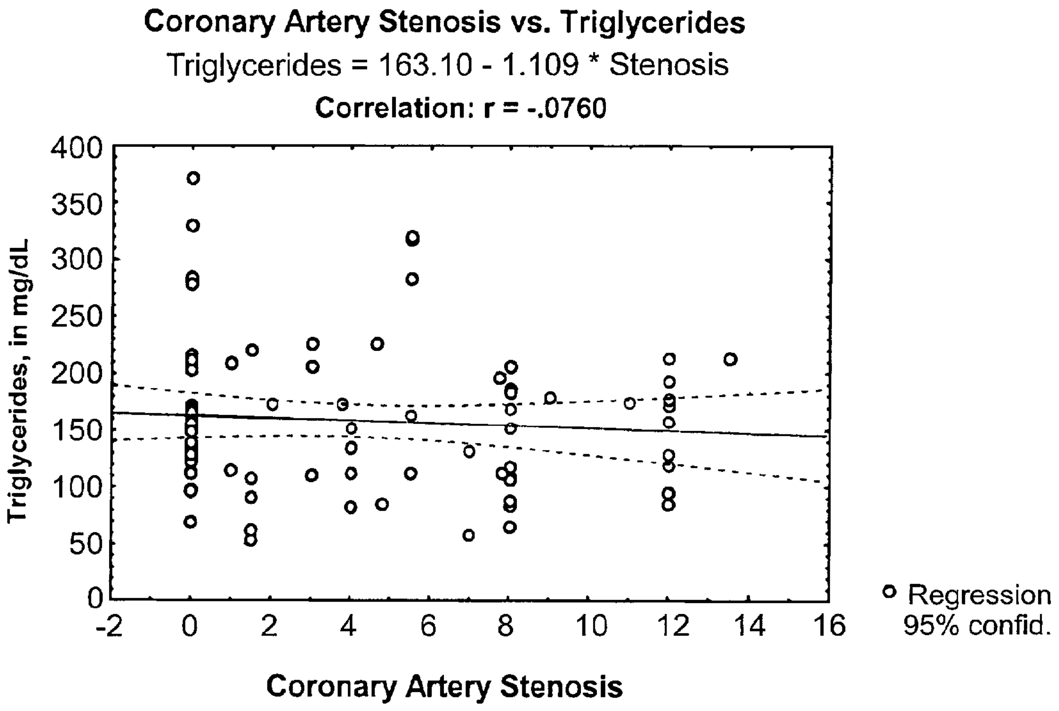
FIG. 6 shows the relationship between the degree of coronary artery stenosis and triglycerides concentration in IHD patient sera.
Figure 7:
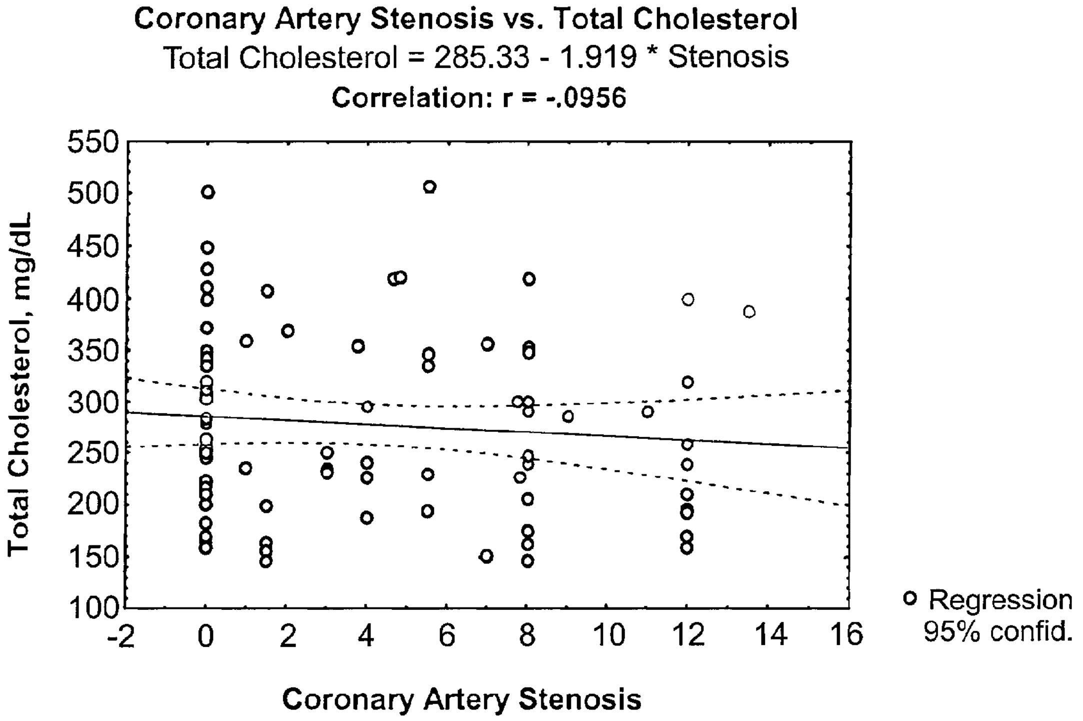
FIG. 7 shows the relationship between the degree of coronary artery stenosis and total cholesterol concentration in IHD patient sera.
Figure 8:
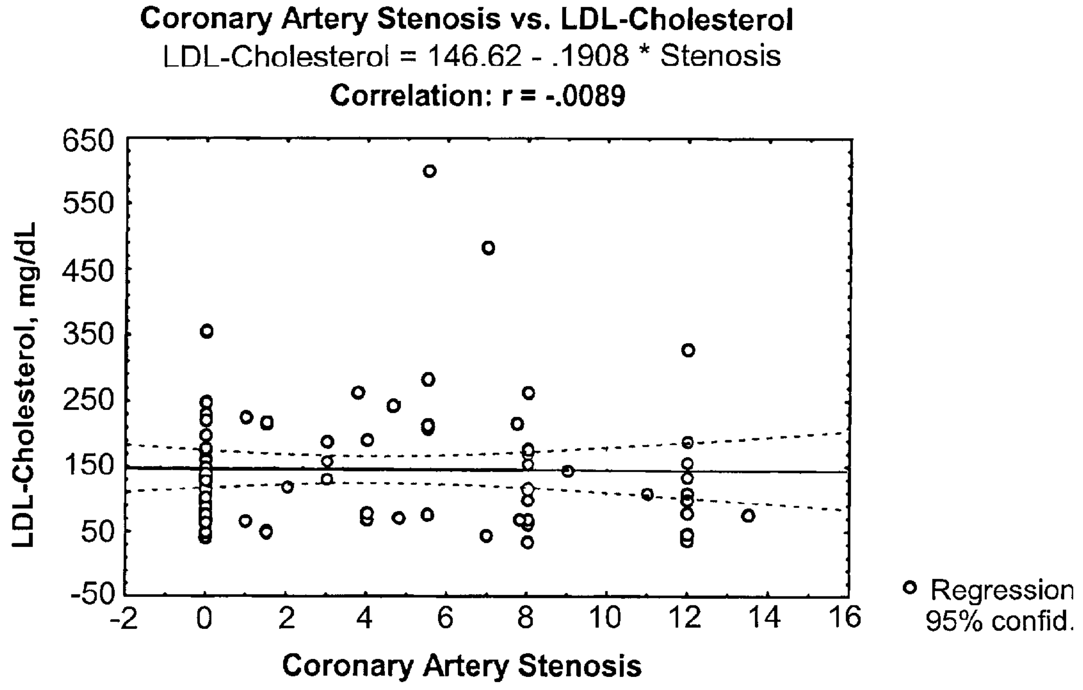
FIG. 8 shows the relationship between the degree of coronary artery stenosis and LDL-cholesterol concentration in IHD patient sera.

No links was observed between the degree of coronary stenosis and such serum lipids as triglycerides, total cholesterol and cholesterol of low density lipoproteins, LDL-cholesterol (FIGS. 6, 7, 8)

Cerebral Artery Stenosis

Figure 9:
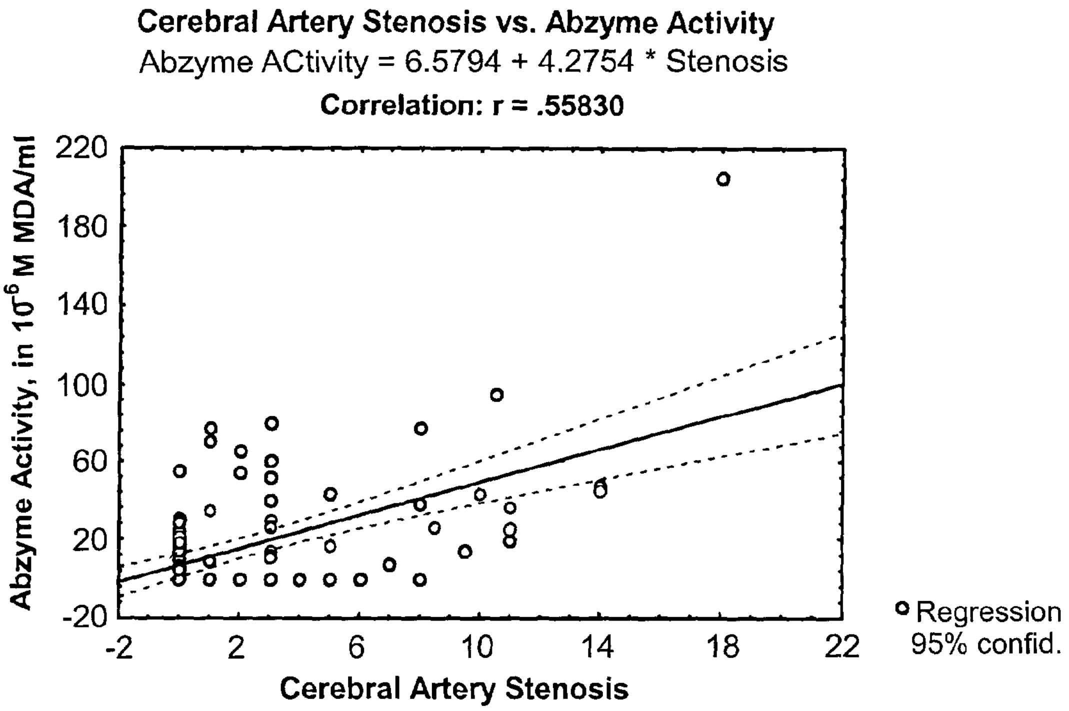
FIG. 9 shows the correlation between the degree of cerebral artery stenosis and the activity of lipid-oxidising anti-*Chlamydia* antibodies in ICD patient sera. Severity of the stenosis is presented in terms of a score, which was calculated as an integral parameter of the stenosis of cerebral arteries estimated by angiography.

A positive significant correlation between level of the abzymes and arterial stenosis was observed in the group of patients with ICD (FIG. 9).

Figure 10:
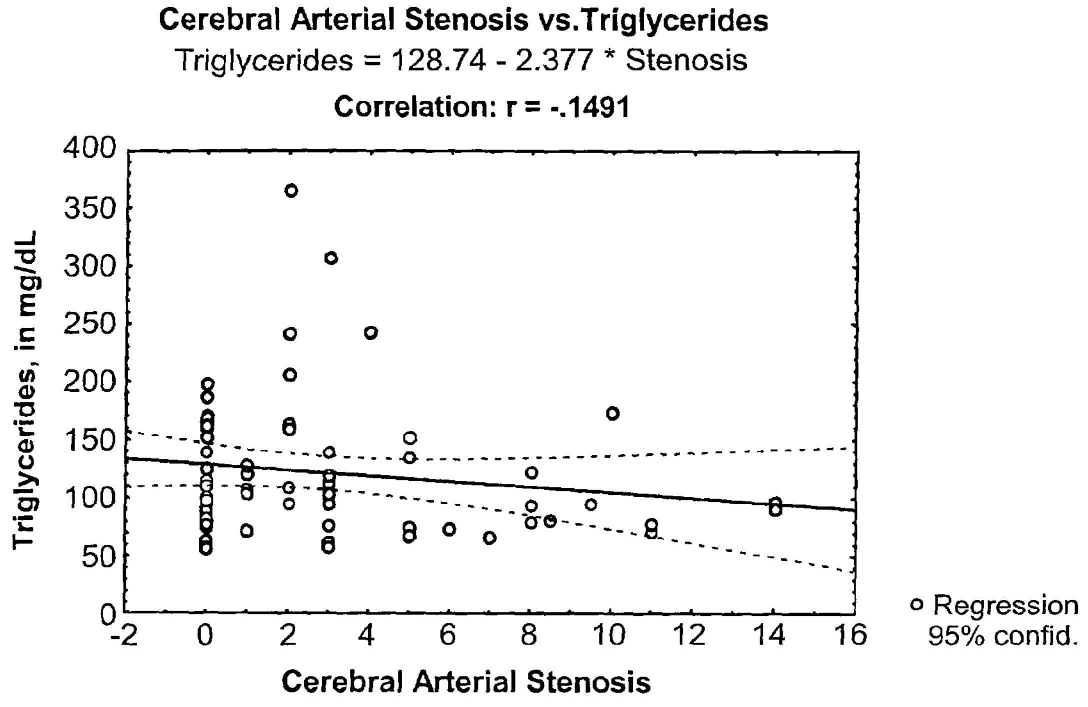
FIG. 10 shows the relationship between the degree of coronary artery stenosis and triglycerides concentration in ICD patient sera.
Figure 11:
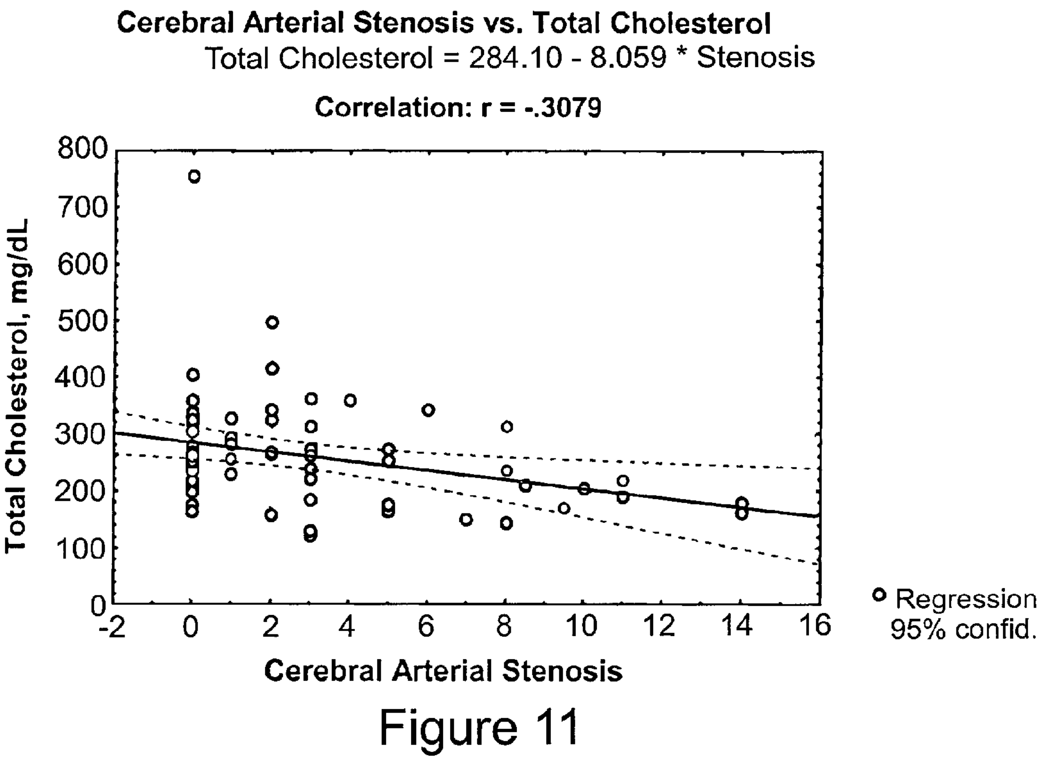
FIG. 11 shows the relationship between the degree of coronary artery stenosis and total cholesterol concentration in ICD patient sera.
Figure 12:
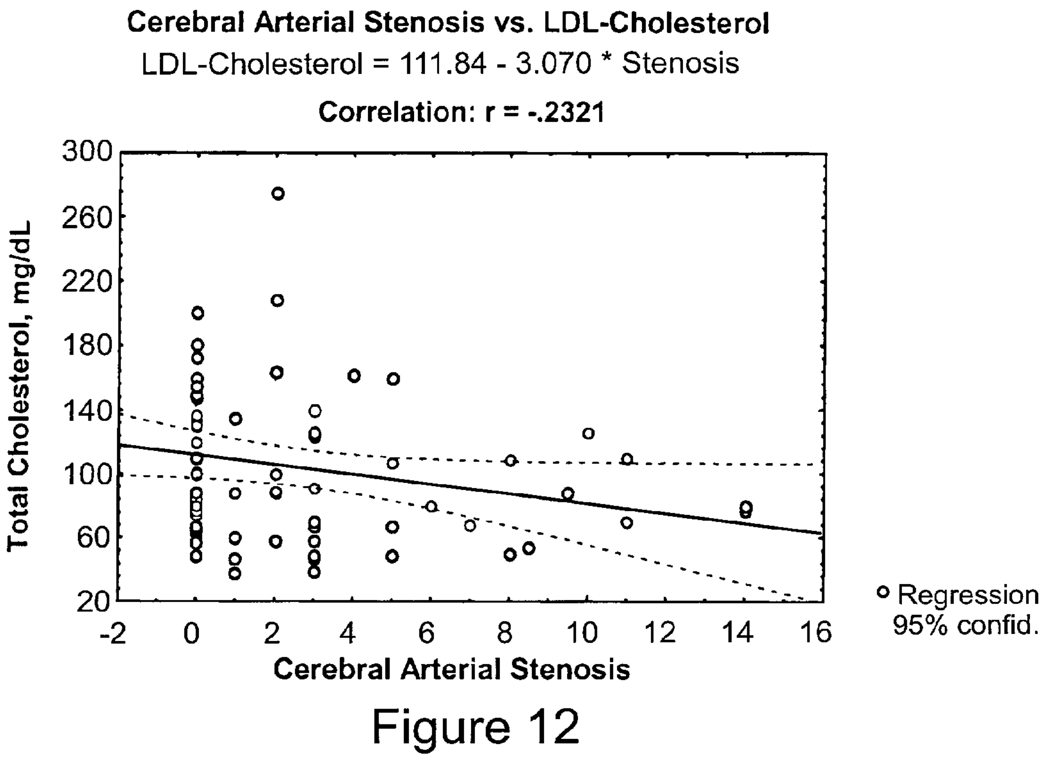
FIG. 12 shows the relationship between the degree of coronary artery stenosis and LDL-cholesterol concentration in ICD patient sera.

As in the IHD patients, in this group there no links were found between the degree of arterial stenosis and serum triglycerides, total cholesterol and LDL-cholesterol (FIG. 10, 11, 12).

These experiments establish a positive link between anti-*Chlamydia* abzyme activity and the degree of stenosis both in heart and brain arteries, and shows that these antibodies are involved both in the initiation and progression of atherosclerosis.

EXAMPLE 6

Inhibition of Abzymes using Acetylsalicylic Acid (Aspirin)

The data presented in Tables 13 and 14 demonstrate that the activity of anti-*Chlamydia* lipid oxidising abzymes can be inhibited by acetylsalicylic acid (aspirin) when it is administered to humans.

Three patients with Coronary Heart Disease (CHD), whose blood had a significant level of abzyme activity of these abzymes, were treated with 250 mg daily dose of aspirin.

After a week, blood tests of these patents revealed a significant inhibition of the abzyme activity: 5-fold for the one patient and an undetectably low level for the other two (Table 13)

To eliminate the possibility that administration of aspirin in the above experiments coincided with the natural clearance of the abzymes from the bodies of the patients and to investigate the in vivo effect of aspirin on anti-Chlamydial lipid oxidising abzymes, the following experiment was undertaken.

A patient F with Silent Myocardial Ischaemia who was taking regularly 250 mg aspirin daily was identified. The level of the abzymes in the blood of patient F was determined and found to be almost undetectable.

Patient F stopped taking aspirin for a week and the level of abzyme in his blood was determined again. A significant level of lipid oxidising abzymes was found in the serum of patient F.

Patient F resumed the previous regime of 250 mg aspirin daily, and the level of abzymes was determined after 7 day. The level of these abzymes was significantly reduced (Table 14) relative to the level when the patient was not receiving aspirin.

During the course of theses experiments, the patient did not have any respiratory disorder, or signs of any other pathological conditions. This indicates that the recorded variations of the abzyme activity were related to the intake of aspirin by this patient.

In conclusion, the present data show that acetylsalicylic acid inhibits lipid-oxidising anti-*Chlamydia* antibodies in vivo, and, in particular, in patients with clinical complications of atherosclerosis.

EXAMPLE 7

Antibodies which Cross-React with Chlamydial Cells

A commercially available preparation of antibodies specific for human Apo-B was tested for ability to cross-react with ovine *Chlamydia psittaci* (Intervet).

Figure 13:
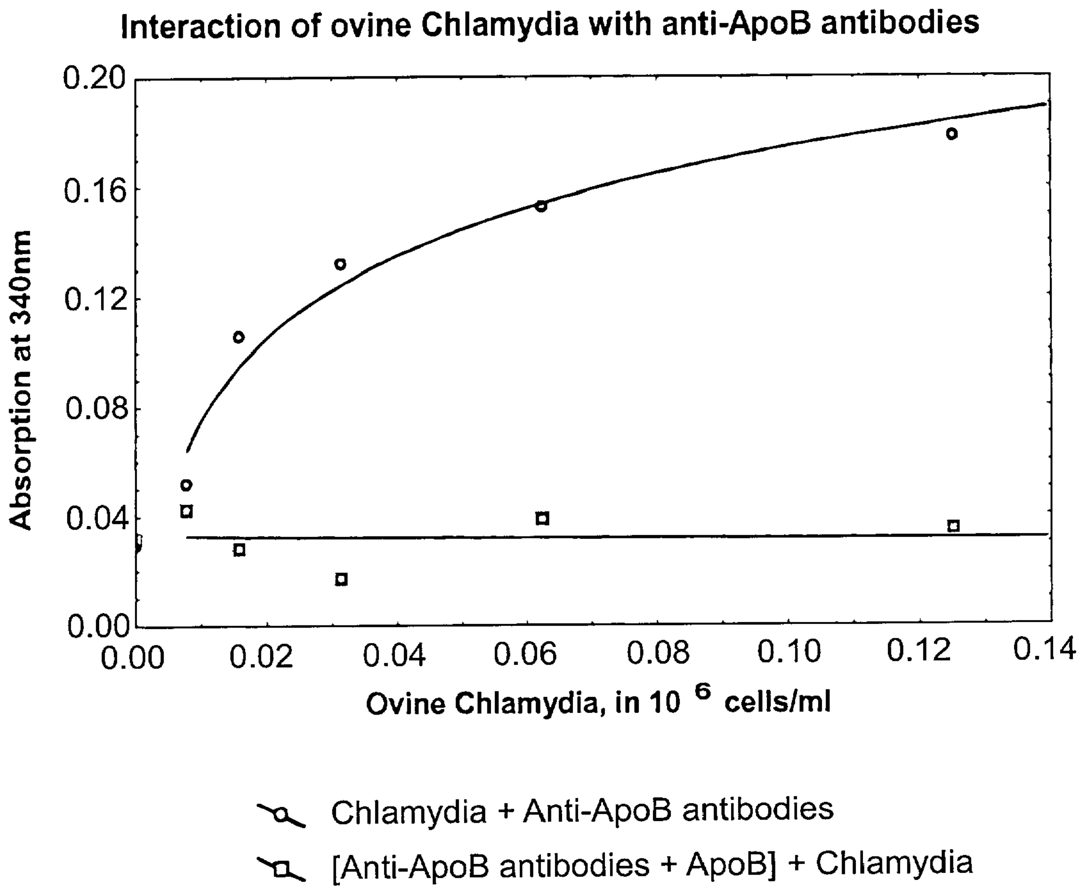
FIG. 13 shows the cross-reaction of anti-apolipoprotein B antibodies with *Chlamydia*.

The anti-apo-B antibody preparation was observed to contain a fraction which also binds to ovine *Chlamydia* (FIG. 13).

Apo-B therefore has an epitope which is identical to an epitope present on the Chlamydial membrane. Antibodies which bind this epitope will cross-react with *Chlamydia* cells and human apo-B.

EXAMPLE 8

The Effect of Anti-Chlamydial Agents on Abzyme Activity in vivo

Patients aged between 45 and 62, with stable angina were treated either with 500 mg azithromycin once per day for 15 days and 30 days or with 500 mg azithromycin, 500 mg, plus aspirin, 250 mg, daily for 15 days.

Abzyme activity before and after treatment is shown for the first group in Table 15 and for the second group in Table 16.

Abzyme activity was shown to be significantly reduced in both groups of patients after 15 days, with the reduction being particularly large in the group treated with azithromycin and aspirin. A reduction in LDL levels was also observed. No adverse reactions were registered in any of the patients.

The clinical condition of patients was also observed to improve over the course of treatment (Table 17).

Administration of the anti-Chlamydial drug azithromycin over two weeks, in particular in combination with aspirin, reduced abzyme activity and improved the clinical condition of patients suffering from angina.

EXAMPLE 9

Abzyme Activity in vivo

Abzyme levels were determined in five sets of people using the methods described herein. A control group were determined to be healthy by present techniques. A silent ischaemia group were individuals who were shown to be ischaemic in an exercise/ECG test but were unaware of any health problems.

Groups of individuals suffering from stable or unstable angina and who had suffered a myocardial infarction were also tested.

The average level of abzymes in each group is shown in Table 18, where n is the number of individuals in each group. Individuals were considered to be positive for abzymes, if a 15% increase in lipid oxidation was observed on addition of *Chlamydia* cells using the methods described herein. The percentage of each group who were positive for abzymes is also shown in Table 18. None of the values in the table has been adjusted for individuals taking aspirin.

The level of abzyme activity and the proportion of individuals testing positive for abzymes is shown to correlate with the severity of the individual's condition. Abzyme activity is observed to drop sharply after a heart attack (compare values for unstable angina and acute phase myocardial infarction). Abzyme activity then rises progressively after the heart attack in surviving patients.

This is indicative of an active role for abzymes in the induction of a myocardial infarction. Abzymes may form part of the agglutination mechanism of the thrombolytic clots which block blood vessels and produce the infarction. This agglutination into clots reduces the detectable abzyme activity in the vascular system. As the clot dissolves post-infarction, detectable abzyme activity increases.

EXAMPLE 10

The Effect of Aspirin on Abzyme Activity in vivo

Abzyme activity was determined in groups of individuals with class I, II and III stable angina or unstable angina using the methods described herein. Individuals were also questioned as to whether they were taking aspirin. Individuals were sub-grouped according to whether they reported taking aspirin and the results are shown in Table 19. These results are not adjusted for individuals taking aspirin but not reporting it.

The figures shown in Table 19 are values of abzyme activity of individuals in each group (i.e. class I aspirin takers and non-aspirin takers etc).

These results show that abzyme levels correspond to the severity of the disease. Aspirin takers generally have lower abzyme activity than non-aspirin takers with the same clinical symptoms.

EXAMPLE 11

Animal Model for Atherosclerotic Disorders

Rabbits were infected with *Chlamydia psittaci* (Lori strain) by the intra-tracheal route with 1.5 mls of 10% suspension of chicken embryo containing $1\times10^{7\ 5}$ of *Chlamydia* cells. The sera of the rabbits was collected at day 0 (pre-infection) and then every 14 days thereafter, by using the standard blood collection route from the heart.

The sera was then used in a standard ELISA assay to measure the titre of anti-*Chlamydia* IgG. On the same sera samples, the amount of *Chlamydia* abzyme level was measured using the standard assay described previously. The appearance of abzymes correlates with the appearance of anti-*Chlamydia* IgG antibodies.

Results for 4 rabbits (3 infected and 1 control) are shown in Table 20.

These results show that an animal model with high abzyme levels can be generated by infection with *Chlamydia* These models are useful in following the progression of disease caused by abzymes and determining various parameters such as rate of clearance. Models are also useful in testing compounds as potential drugs for the reduction of abzyme levels and concomitant improvement in symptoms.

EXAMPLE 12

Anti-*Chlamydia* Abzymes in Rabbits

The production of lipid-oxidising anti-*Chlamydia* antibodies was demonstrated using a rabbit model produced as described above by intra-tracheal infection with *Chlamydia Psittaci.*

Results are shown in Table 21. Rabbits were infected intra-tracheally with 1.5 ml of 10% suspension of chicken embryo containing $1\times10^{7.5}$ of *Chlamydia Psittaci* (Lori strain) and blood was collected from the rabbit hearts. Abzyme levels on $7^{th}$ day after a subcutaneous injection of a vaccine, formalin treated $1\times10^{7\ 5}$ of *Chlamydia Psittaci* (Lori strain) are shown (§ table 21).

The appearance of abzymes coincided with the accumulation of anti-*Chlamydia* IgG detected as detected by ELISA. An injection of the same bacteria, but in formalin treated preparation, on the $14^{th}$ day of the infection (rabbit 3) led to an increase in the ELISA anti-*Chlamydia* IgG titers on the $7^{th}$ day after this inoculation. At the same time, in the serum of this rabbit there was a 2-fold reduction in the abzyme activity, from 131 to 64 μM MDA/ml.

There was no such reduction in the abzyme activity registered for two other rabbits, which did not receive this inoculation.

Inoculation of the vaccine preparation of the *Chlamydia* antigen was thus observed to reduce the presence/activity of anti-*Chlamydia* abzymes.

EXAMPLE 13

Anti-Abzyme Therapy in Ischaemic Heart Disease

A group of 30 patients with ischaemic heart disease (IHD) was selected for experimental therapy to reduce/eliminate the activity of anti-*Chlamydia* abzymes in their serum (the therapy group) and a group of 20 'matched' patients were not treated (the untreated Patient Control Group). The trial took place in Saratov Cardiological Centre (Russian Federation) from June until August 2002.

The therapy group comprised 23 male and 7 female patients with an average age of 55±1.1 years. The patients control group for monitoring of the abzyme level comprised 20 patients with IHD, of which 15 were male and 5 were female patients with an average age of 53±1.2 years. Each patient gave written consent for his/her participation in the trial.

All patients had angina of II–III class of Canadian Cardiological Society classification. 15 patients in the therapy group and 10 in the patient control group had a history of myocardial infarction in the past year. IHD diagnosis for the other 15 patients in the first group and 10 in the patient control group was confirmed by coronary angiography, which detected 70% or more of arterial stenosis.

Apart from the degree of the generalization or severity of atherosclerosis, all groups were matched not only on age, gender and risk factors but also on medication, nitrates, β-blockers, angiotensin-converting enzyme inhibitors etc.

The progression of the clinical condition of the patients was monitored by the use of the modified Bruce Protocol for treadmill exercise/stress ECG testing and on the Rose-Blackburn Questionnaire (Cardiovascular Survey Methods. WHO, Geneva, 1968)

The main parameter of the selection of a patient for the trial was a level of anti-*Chlamydia* abzyme activity in excess of 15 μM of malondialdehyde (MDA) per ml of serum. The therapy group was split into 4 therapeutic sub-groups:

1.) Therapy group A—those given a nonspecific inhibitor of anti-*Chlamydia* abzymes, azithromycin, which also has anti-microbial properties, was prescribed in the dose of 500 mg daily.
2.) Therapy group B—a combined administration of azithromycin, in the same dose, with acetylsalicylic acid (aspirin) was prescribed. The latter has the apparent ability to block specifically the abzymes via chelating ions of copper in their active centre. The dose of aspirin was 250 mg per day.
3.) Therapy Group C—a combined administration of two types of nonspecific inhibitors of the abzymes with antioxidant properties, anti-microbial azithromycin, in the same dose as in the previous groups, and vitamins E, A, C, was prescribed The daily dose of vitamin E was 30 mg, vitamin A 1,500 EU and vitamin C 90 mg.
4.) Therapy Group D—The patients in this group were given 250 mgs aspirin daily only.

The blood of the patients of all three groups was tested every two weeks. The therapies were continued subject to the efficiency of the suppression/elimination of the anti-*Chlamydia* abzyme activity and the trial results are shown up to up to 60 days after administration of placebo/therapy.

The titre of anti-*Chlamydia* antibodies was measured in the Therapy group using the method previously described (see Table 26). The severity of clinical symptoms was also measured (see Table 28)

Results of the monitoring of the suppression of the anti-*Chlamydia* abzyme activity are presented in the following tables (Tables 22–27).

At first it was noticed that in two weeks of the therapy in all groups there was a significant reduction in the abzyme activity. The most prominent was in the Therapy Group B where the use of a nonspecific inhibitor, azithromycin, was combined with use of a specific inhibitor, aspirin (Table 23). Indeed, the level of the activity in this group reached the level of clinically healthy individuals (see Summary Table 28). An important observation was that patient TGB7 in this group showed a large increase in abzyme level (which correlated with a worsening of clinical symptoms) on the $45^{th}$ hday (double asterix—Table 23) and then after another 15 days of treatment the patient started to feel better and abzymes had reduced to 0. TGB7 also showed an increase in ApoB levels (asterix—see Table 7) at the same time as an increase in abzymes level at 45 days.

The least effective therapy was in the Therapy Group A (azithromycin only—Table 22) where for 27% of the patients (3 out of 11, marked with an asterix) there were no changes in the abzyme activity after 15 days. However, a continued reduction for the majority of the patients was reversed for two of them in the first group on the $30^{th}$ day of the trial (TGA2 and TGA6, Table 1, marked with two asterixes). This observation, together with the fact that there were some patients with, although reduced, a remaining significant level of the abzyme activity, led to the extension of treatment for another 30 days, resulting in significant decreases in all patients. In therapy group A clinical symptoms of patients TGA2 and TGA6 improved for 15 days and correlated with a reduction in the abzyme level, however clinical symptoms worsened and abzymes level increased around the $30^{th}$ day of the trial (double asterix—Table 22).

In Therapy Group C (Azithromycin and antioxidants) there was one patient (TGC1) who showed no decrease in abzyme activity (asterixed—Table 24)

The use of aspirin alone, in the prescribed dose, without azithromycin, led to a reduction in the abzyme activity but to a lesser degree than observed with the combination (Therapy Group D—Table 25).

The applied anti-abzyme therapy has significantly improved the clinical condition of the majority of the patients, which was evaluated with the modified Rose-Blackburn Questionnaire (Table 27) and verified by the use of the treadmill exercise/stress ESG testing At the same time there was no positive clinical dynamic noticed in the control group, even for a single patient. In Table 27 PCG indicates Patient Control Group, § indicates results obtained by immuno-fluorescent assay, §§ indicates results obtained by immuno-enzymatic assay, §§§ indicates results obtained by immuno-turbidimetric assay. * indicates a statistically significant difference.

No statistically significant changes were observed for the following parameters of coagulation: Kaolin Clotting Time, activated Partial Thromboplastin Time, Prothrombin time. There were no changes registered in the level of the serum Creatinine and the liver enzymes Alanine aminotransferase and Aspartate aminotransferase.

No patients in the experimental therapy groups had had positive changes in their clinical conditions for a number of months/years prior to their selection for the trial. Therefore, this absence of positive dynamic can be used as the ‘internal’ control for the significant clinical progress of the patients which has been observed.

The original intensive regimen of abzyme inhibitor, which has anti-microbial properties, totally eliminated the presence of anti-*Chlamydia* IgG.

By targeting the anti-*Chlamydia* abzymes, significant improvements in lipid concentrations and thrombosis were achieved (Table 27) Therefore, it is possible to suggest that the developing abnormalities in the lipid metabolism and coagulation system in atherosclerosis are secondary to the appearance of these lipid-oxidising catalytic antibodies.

The observed beneficial effect of azithromycin could not be explained by its anti-bacterial properties because only in 15 patients out of 30 (in 50%) selected for the trial had beforehand tested positive on the presence of *Chlamydia* infection. The level of anti-*Chlamydia* IgG in the serum of another 8 patients was insignificant, below 1:32 in immuno-fluorescent assay. The other 7 patients tested negative.

The diagnostic test indicates whether a patient carries abzymes and is not necessarily correlated with the patient being positive for *Chlamydia* IgG antibodies. Therefore, the therapy should not be prescribed on the basis of seropositivity for *Chlamydia*. This shows the usefulness in the invention when the diagnostic test is linked to administration of the correct therapy followed by repeated prognostic tests to monitor clearance of abzymes using the treatment.

Certain IHD patients in the theranostic trial were negative for anti-*Chlamydia* IgG antibodies but tested positive for abzymes. The abzyme and Rose-Blackburn Test scores before and after treatment for these patients are shown in shown in table 29. These patients were treated and their abzyme activity reduced with a subsequent improvement in clinical symptoms.

These results show that whether a patient carries abzymes is not necessarily correlated with the patient being positive for *Chlamydia* IgG antibodies. An atherosclerotic condition cannot be diagnosed or therapy prescribed on the basis of seropositivity for *Chlamydia*. However, abzymes are shown to be useful as a diagnostic marker of atherosclerotic conditions and may be linked to administration of the appropriate therapy followed by repeated prognostic tests to monitor clearance of abzymes.

EXAMPLE 14

Anti-Abzyme/Antioxidant Properties of Azithromycin

The inhibitory activity of Azithromycin on abzymes isolated from an atherosclerotic lesion was measured as described above. The results are shown in Table 30. Each number is a mean of duplicate/triplicate measurement, and calculated as a difference between the level of MDA accumulation in the tested serum before and after the addition of 0.5 of immunisation dose of ovine *Chlamydia* vaccine ('Intervet'). The effect of DMSO was deducted from the readings where indicated (**).

Azithromycin was found to be a strong in vitro inhibitor of abzyme activity. This activity may be responsible for the in vivo biological effects observed with azithromycin, such as the rapid decrease in abzyme activity after administration of azithromycin.

EXAMPLE 15

Membrane Integrity of *Chlamydia* and Abzyme Activity

Abzyme activity was measured as described above using formalin, ammonium sulphate or SDS treated samples of *Chlamydia pneumoniae* or *Chlamydia Psittaci.* In these reactions, no lipid oxidising reaction in the test system.

Treatment of the *Chlamydia* bacteria with chaotropic agents, including non-ionic detergents 1% Triton X-100 and Igepal CA-630, 10% solution of DMSO, which preserve the presence of the membrane lipids in the system but disrupt the integrity of the bacterial membrane, completely abrogated the development of lipid oxidation reaction.

These experiments indicate that lipids are important for the initiation and the development of the reaction(s) of lipid peroxidation developing in the test system. In particular, a role for lipopolysaccaride, which is disrupted by the above treatments, is indicated.

EXAMPLE 16

Case Histories

CASE No 1

A 64 year old male patient was diagnosed with Ischaemic Heart Disease 3 years ago when he had the first symptoms of angina pectoris. The diagnosis was confirmed by coronary angiography, which established a stenosis of two arteries: 75% of the right coronary artery and 100% occlusion of the anterior intraventricular artery.

He was selected for the theranostic trial on the grounds that abzymes were detected in his serum. A combination of two abzyme inhibitors, azithromycin, in the dose of 500 mg daily, and aspirin, in the dose of 250 mg daily His level of anti-*Chlamydia* IgG was high with a titer of 1:256.

Before the treatment his clinical condition, estimated by a score of a modified Rose-Blackburn protocol, was 19. The abzyme activity was 25 μM MDA/ml, the level of total cholesterol 226 mg/dL, triglycerides—90 mg/dL, HDL-cholesterol—56 mg/dL, LDL-cholesterol—73 mg/dL, ApoA—139 mg/dL, ApoB—81 mg/dL, alanine aminotransferase (ALT)—25 U/L, aspartate aminotransferase (AST)—29 U/L, creatinine—0.71 mg/dL.

During the treatment there were no significant adverse reactions noticed. On his first visit after the start of the therapy, 15 days, he reported a certain improvement in the signs of his disease. This improvement continued until the $30^{th}$ day of the therapy. This was supported by an increase in the tolerance time during treadmill exercise ESG testing by modified Bruce Protocol.

At that time neither the abzyme activity nor the presence of anti-*Chlamydia* IgG was detected in his serum. The level of lipid parameters also improved: total cholesterol reduced to 172 mg/dL, triglycerides to—80 mg/dL, HDL-cholesterol—52 mg/dL, LDL-cholesterol—64 mg/dL, ApoA—110 mg/dL, ApoB—67 mg/dL. The level of ALT, AST and creatinine remained the same—25 U/ml, 27 U/ml and 0.7 mg/dL respectively.

On the arrival of the $45^{th}$ day from the beginning of the therapy he reported that a week before, on the $38^{th}$ day from the beginning, his condition had started to deteriorate—the frequency and intensity of the angina attacks had suddenly increased. This coincided with a rise in abzyme activity, which reached 80 μM MDA/ml. However, it is important to note, no 'traditional' anti-*Chlamydia* IgG were registered.

At the same time, the parameters of the lipid metabolism also deteriorated: total cholesterol increased to 185 mg/dL, triglycerides—143 mg/dL, LDL-cholesterol—74 mg/dL, ApoA—115 mg/dL, ApoB—87 mg/dL. Level HDL-cholesterol and ApoA remained essentially the same—50 mg/dL and 115 mg/dL, correspondingly. An important observation was that the level of liver enzymes also changed, ALT increased to 35 U/L and AST to 39 U/L; creatinine concentration was 0.8 mg/dL.

However, continued therapy seemed to completely suppress/eliminate the abzyme activity, which was also accompanied by an improvement in the concentration of some lipid parameters: total cholesterol was reduced to 165 mg/dL, triglycerides to—100 mg/dL, mg/dL. Concentration of HDL—cholesterol was 47 mg/dL, LDL-cholesterol 72 mg/dL, ApoA—112 mg/dL. The level of ALT, AST and creatinine became 24 U/ml, 25 U/ml and 0.7 mg/dL respectively.

At the same time the ApoB level remained on the pre-treatment level 80 mg/dL. The initially improved clinical condition also returned to the level that it was before the beginning of the therapy, the Rose-Blackburn score was 19. To stabilise the suppressed level of the abzymes with an attempt to improve the clinical parameters of the patient, it was recommended to continue the prescribed anti-abzyme therapy.

No anti-*Chlamydia* IgG was detected in this patient from the $15^{th}$ day of the start of the therapy onwards and the continued use of azithromycin was aimed at controlling the suppressed level of the cross-reacting abzymes, which bind and oxidise lipoproteins, rather than bacterial infection per se.

Case No.2

A 46 year old male patient was diagnosed with IHD when he was admitted with an acute myocardial infarction on 21 Feb. 2002. Before that he had no history of heart disease. The following May a coronary angiography revealed no stenosis/narrowing of his coronary arteries.

This patient was selected for a theranostic trial on the grounds that significant activity of the anti-*Chlamydia* abzymes was detected in his serum. It was 140 μM MDA/ml. A combination of two types of abzyme inhibitors, azithromycin, in the dose of 500 mg daily, and an antioxidant cocktail of vitamins E, A, C, was prescribed. The daily dose of vitamin E was 30 mg, vitamin A 1,500 EU and vitamin C 90 mg.

There was no detectable level of 'traditional' anti-*Chlamydia* IgA, IgG or IgM detected in the serum of this patient before or during the treatment period.

Before the treatment his clinical condition, estimated by the score of a modified Rose-Blackburn protocol, was 17. The level of total cholesterol was 205 mg/dL, triglycerides—129 mg/dL, HDL-cholesterol—39 mg/dL, LDL-cholesterol—80 mg/dL, ApoA—152 mg/dL, ApoB—221 mg/dL.

During treatment no significant adverse reactions were noticed. He started to feel a certain improvement in signs of the disease after the first two weeks of the treatment. This progress continued through the whole period of the therapy of 60 days. This was supported by a significant increase in the tolerance time during treadmill exercise ESG testing carried out in accordance with modified Bruce Protocol.

At the end of the observation period, after 60 days, neither the abzyme activity nor the presence of anti-*Chlamydia* IgG was detected in his serum.

These changes in abzyme activity coincided with a significant improvement in the clinical condition of the patient. His score on the modified Rose-Blackburn protocol reduced from 17 before the treatment to 13 after it.

EXAMPLE 17

Effect of Anti-Abzyme Therapy on Thrombosis

One of the indicators of atherosclerotic disorders is that patients often present with aberrations in the time it takes for their blood to form clots (this is generally increased in patients). A number of pathways can lead to clot formation and therefore there are four internationally recognized tests for clotting time. The first is called Activated Partial Thromboplastin Time (APTT) and works by adding thromboplastin and calcium to measure the intrinsic pathway. The second called Prothombin Time (PT) is a simple measurement for the extrinsic pathway. Silica clotting time (SCT) measures clotting induced by fine particles (silica) and Kaolin Clotting Time (KCT) measures clotting induced by larger particles (Kaolin). For all these fast clotting times are indicative of higher risk of thrombosis.

Before treatment, the clotting times using all four methods for all patients in all therapy groups were measured and the mean calculated with a standard error. Measurements were repeated 60 days later. Controls were our Patient Control Group (measurements taken once—values did not change significantly for these patients over time) and also form our clinically healthy control group. The results of treatment are shown in Table 32.

The average value for patients before treatment for the APTT test was 22.4±0.89 (comparable with the Patient Control Group value of 25.2±1.37) and was significantly different from the clinically healthy group value of 49.1±7. After treatment the patients had a mean value of 46.9±6.45 and was therefore within the 'normal range' of clotting times i.e. had been normalized.

The average value for patients before treatment for the PT test was 13.5±0.94(comparable with the Patient Control Group value of 17.3±4.05) and lower than the clinically healthy group value of 23.7±4.01. After treatment the patients had a mean value of 25.3±4.05 and was therefore within the 'normal range' of clotting times i.e. had been normalized.

The average value for patients before treatment for the SCT test was 151±15.0 (comparable with the Patient Control Group value of 137±11.5) and significantly lower than the clinically healthy group value of 248±10.0. After treatment the patients had a mean value of 235±17.9 and was therefore within the 'normal range' of clotting times i.e. had been normalized.

The average value for patients before treatment for the KCT test was 51.2±4.59(comparable with the Patient Control Group value of 50.3±2.16) and was significantly different from the clinically healthy group mean value of 133±23.7. After treatment the patients had a mean value of 126±34.2 and was therefore within the 'normal range' of clotting times i.e. had been normalized.

These results show that anti-abzyme therapy can be used to normalize clotting times (using all Internationally recognized clotting time assays) and reduce the risk of thrombosis and hence heart attack and stroke.

TABLE 1

| IgG from human atherosclerotic lesion, in μg | Lipid peroxidation, in μM MDA per ml: +10 μl ovine Chlamydia | +2.5 μl feline Chlamydia |
|---|---|---|
| 0 (control) | 3 ± 0.4 | 0 ± 0.3 |
| 0.18 | 6 ± 1.1 | 2 ± 0.7 |
| 0.36 | 2 ± 1.2 | 0 ± 0.5 |
| 0.57 | 10 ± 0.9 | 1 ± 0.2 |
| 0.8 | 18 ± 1.0 | 0 ± 0.4 |
| 1.35 | 19 ± 0.7 | 0 ± 0.5 |
| 1.8 | 26 ± 1.3 | 0 ± 0.8 |
| 5.4 | | 4 ± 0.3 |
| 8.0 | | 23 ± 1.5 |

TABLE 2

| Tested systems | Lipid peroxidation in serum, in μM MDA/ml: without Chlamydia | +10 μl ovine Chlamydia |
|---|---|---|
| Lipoproteins + antibodies (1st control) | | |
| Serum lipoproteins | 130 ± 9.43 | 193 ± 19.9 |
| +1 μg/ml of lesion IgG* | 246 ± 17.5 | 342 ± 8.52 |
| Only antibodies (2nd control) | | |
| Lipoprotein removed from serum by ultracentrifugation +1 μg/ml lesion IgG* | 29 ± 3.57 | 63 ± 5.42 |
| Removal of antibodies by pre-absorption with serum lipoproteins | | |
| Serum was initially incubated with 1 μg/ml of lesion IgG* and then lipoproteins were removed by ultracentrifugation | 35 ± 4.66 | 23 ± 1.71 |

TABLE 3

| Serum | Control serum, MDA in μM/ml | Patient No3' serum, MDA in μM/ml |
|---|---|---|
| Initial level | 58 ± 4.5 | 187 ± 5.0 (100%) |
| +6.25 μl feline Chlamydia | 50 ± 2.8 | 225 ± 9.9 (120%) p < 0.05 |

TABLE 4

| | Control' serum, MDA in μM/ml | | | Patient No2' serum, MDA in μM/ml | | |
|---|---|---|---|---|---|---|
| | Initial | +ovine Chlamydia | | Initial | +ovine Chlamydia | |
| Samples | level | 10 μl | 100 μl | level | 10 μl | 100 μl |
| Serum | 56 ± 6.4 | 58 ± 5.0 | 48 ± 6.6 | 128 ± 9.0 (100%) | 202 ± 13.4 (158%) p < 0.01 | 580 ± 24.2 (453%) p < 0.001 |
| Serum-IgG | 52 ± 6.2 | 60 ± 6.6 | 62 ± 7.2 | 76 ± 4.4 | 72 ± 6.8 | 96 ± 8.4 |

TABLE 5

| Cases | Lipid peroxidation in μM MDA per 1 ml of serum: Before the addition of Chlamydia* | After the addition of Chlamydia* | Increment |
|---|---|---|---|
| Control: K | 58 | 90 | 32 |
| K1 | 104 | 124 | 20 |
| K2 | 124 | 148 | 24 |
| K3 | 131 | 168 | 37 |
| K4 | 106 | 124 | 18 |
| M | 112 | 108 | -4/0 |
| M1 | 70 | 70 | 0 |
| M2 | 78 | 86 | 8 |
| M3 | 102 | 80 | -22/0 |
| M4 | 84 | 76 | -8/0 |
| | 1/10 or 10%<br>96 8 ± 3.99 (n = 10) | 1/10 or 10%<br>108 ± 5.73 (n = 10) $p_{(*Chlamydia)} > 0.05$ | 13.9 ± 5.14 (n = 10) |
| Patients 1 | 116 | 166 | 50 |
| 4 | 86 | 106 | 20 |
| 5 | 122 | 168 | 46 |
| 6 | 40 | 62 | 22 |
| 6a | 208 | 336 | 128 |
| 7 | 118 | 166 | 48 |
| 8 | 82 | 98 | 16 |
| 9 | 160 | 290 | 130 |
| 10 | 60 | 80 | 20 |
| 11 | 236 | 368 | 132 |
| 12 | 256 | 328 | 72 |
| 13 | 174 | 350 | 176 |
| 14 | 168 | 306 | 138 |
| 15 | 126 | 162 | 36 |
| 16 | 290 | 290 | 0 |
| 17 | 246 | 342 | 96 |
| 18 | 270 | 376 | 106 |
| 19 | 156 | 272 | 116 |
| 20 | 164 | 312 | 148 |
| 21 | 206 | 344 | 138 |
| 22 | 290 | 332 | 42 |
| | 13/21 or 62%<br>170 ± 10.8 (n = 21) $p_{(control)} < 0.001$ | 17/21 or 81%<br>250 ± 15.0 (n = 21) $p_{(control)} < 0.001$ $p_{(*Chlamydia)} < 0\ 01$ | 80 0 ± 13.1 (n = 21) $p_{(control)} < 0.001$ |

TABLE 6

| LDL, 480 μg of protein | Level of MDA production by 0.82 μg of lesion IgG, in μM |
|---|---|
| Control | 0.49 ± 0.023 |
| +0.1 M sodium formate | 0 |
| +0.1 mM ascorbic acid* | 0 |

TABLE 6-continued

| LDL, 480 μg of protein | Level of MDA production by 0.82 μg of lesion IgG, in μM |
|---|---|
| +0.1 M benzoic acid | 0 |
| +1% DMSO* | 0 |

*Antioxidants approved by for use in humans in most developed countries.

TABLE 7

| Metals | Chelators | Proprietary Preparations |
|---|---|---|
| $Fe^{+2}/Fe^{+3}$ | Desferri-oxamine Mesylate | Canad.: Zinecard, Fr.: Cardioxane; Ital.: Cardioxane; Eucardion; USA: Zinecard |
| | Haem Derivatives | Austral.; Panhematin, Fr.: Normosang; USA: Panhematin |
| $Cu^{+1}/Cu^{+2}$ | Penicillamine | Aust.: Artamin; Distamine, Austral.: D-Penamine, Belg.: Kelatin, Canad.: Cuprimine; Depen; Fr.: Trolovol; Ger.: Metacaptase, Trisorcin, Trolovol; Irl.: Distamine; Ital.: Pemine; Sufortan; Neth.: Cuprimine, Distamine; Gerodyl; Kelatin; Norw. : Cuprimine; S.Afr.: Metaalcaptase; Spain: Cuprein; Sufortanon; Swed.: Cuprimine; Switz.: Mercaptyl; UK: Distamine, Pendramine; USA: Cuprimine, Depen. |
| | Tiopronin | Fr.: Acadione; Ger.: Captimer, Ital.: Epatiol, Mucolysin; Mucosyt; Thiola; Tioglis; Spain: Sutilan; Switz.: Mucolysin; USA: Thiola. Multi-ingredient: Ital.: Mucolysin Antibiotico; Spain: Hepadigest. |
| | Trientine Dihydrochloride | USA: Syprine. |
| | Diethyldithio-carbamate | |
| | Acetylsalicylic acid | |

TABLE 7-continued

| Metals | Chelators | Proprietary Preparations |
|---|---|---|
| $Me^{+2}$* | Disodium/ Trisodium Edetate | Fr.: Chelatran; Tracemate; Irl.: Limclair; UK: Limclair, USA: Disotate; Endrate Multi-ingredient; Canad.: Murine Supplement Tears; Fr.: Vitaclair; Ger.: Complete, Duracare; Oxysept; UK: Uriflex G; Uriflex R. |
| | Edetic Acid | Multi-ingredient: Ital.: Conta-Lens Wetting; USA: Summer' sEve Post-Menstrual, Triv, Vagisec Plus; Zonite |
| | Unithiol | Ger.: Dimaval; Mercuval. |
| Other metals of transient valence | | |

*Any bivalent metal

TABLE 8

| Antibacterial agents | Proprietary Preparations |
|---|---|
| Tetracycline | Aust: Achromycin; Actisite; Hostacyclin, Latycin, Steclin; tetrarco; Austral.: Achromycin; Achromycin V, Latycin, Mysteclin; Panmycin P; Steclin-V; Tetramykoin; Tetrex; Belg.: Hostacucline, Canad.: Achromycin; Achromycin V; Apo-Tetra; Novo-Tetra; Nu-Tetra, Tetracyn; Fr.: Florocycline; Hexacycline, Tetramig; Ger.: Achromycin; Akne-Pyodron Kur; Akne-Pyodron oral, Dispatetrin; Hostacyclin; Imex; Quimocyclin N; Sagittacin N, Steclin; Supramycin; Tefilin; Tetrabakat; Tetrablet; Tetracitro S; Tetralution; Ital.: Acromicina; Ambramicina; Calociclina; Ibicyn; Spaciclina; Tetra-Proter; Tetrabioptal; Tetrafosammina, Neth.: Tetrarco; S.Afr.: Achromycin; Arcanacycline; Gammatet; Hostacycline; Rotet; Tetrex; Spain; Actisite, Ambramicia, Britaciclina; Kinciclina; Quimpe Antibiotico; Tetra Hubber, Tetralen; Tetrarco Simple; Swed.: Achromycin; Actisite; Switz.: Achromycine; Actisite, Servitet; Tetraseptine; Triphacycline; UK: Achromycin; Economycin; Sustamycin. Tetrabid-Organon; Tetrachel; USA: Achromycin V; Achromycin; Actisite, Nor-Tet, Panmycin; Robitet Robicaps; Sumycin; Teline; Tetracap; Tetralan, Tetram.* |
| Erythromycin | |
| Azithromycin | |
| Roxithromycin | |
| Ofloxacin | |
| Clinafloxacin | |
| Ciprofloxacin | |
| Clindamycin | |
| Doxycycline | |
| Minocycline | |

*Multi-ingredient: numerous preparations

TABLE 9

| Antioxidants | Proprietary Preparations: |
|---|---|
| Alpha-Tocopherol | Aust.: Avigilen; Ephynal; Etocovit; Evit, Evitol, Tetefit Vitamin E, Austral: Alpha Keri Silky Smooth; Bioglan Micelle E; Bioglan Natural E; Bioglan Water Soluble E; Chew-E; Dal-E; Invite E Forte, Invite E, Marco E; Mega E; Megavit Natural E, Belg.: Ephynal, Canad.: Aquasol E; Novo E; Organex; Vita-E; Fr.: Ephynal; Tocalfa; Toco; Tocomine, Ger.: Antioxidants E; Biopto-E; Detulin; E-Muslin; E-Vicotrat, Ecoro; Embial; Ephynal; Pexan E; Puncto E; Sanavitan S; |

TABLE 9-continued

| Antioxidants | Proprietary Preparations: |
|---|---|
| | Tocorell, Tocovenos, Tocovital; Togasan; Vitagutt Vitamin E; Irl.: Ephynal; Ital.: E Perle; E-Vit; E-Vitum; Ephynal; Evasen Cream, Evion; Evitina; Fertilvit; Na-To-Caps; Tocoferina E; Tocoferolo Bioglan, Tocogen; Viteril; Norw.: AFI-E; Ido-E; S. Afr.: Ephynal; Spain: Auxina E, Ephynal; Glutaneurina B6 Fte; Swed.: Ephynal; Opto Vit-E; Vitacim, UK; Bio E, Ephynal; Praire Gold; Vita-E; USA: Amino-Opti-E; Aquasol E; Aquavit-E, Vita-Plus E; Vitec* |
| Mannitol | Aust.: Osmofundin 20%, Austral.: Mede-Prep; Osmitrol; Canad.: Osmitrol, Fr.; Manicol; Ger.: Eufusol M 20; Mannit-Losung; Osmoofundin 15%; Osmosteril 20%; Thomaemannit; Ital.: Isotol, Mannistol; Switz.: Mannite; USA: Osmitrol; Resectisol.* |
| Silidianin | Aust.: Apihepar.; Biogelat leberachutz, Hepar Pasc Mono; Legalon; Silyhexal; Austral.: Herbal Liver Formula; Liver Tonic Capsules, Prol.; Belg.: Legalon SIL; Fr.: Legalon; Ger.: Alepa; Ardeyhepan N, Carduus-monoplant; Cefasliymarin, Divinal-Hepa, Durasilymarin; Hegrimarin; Heliplant; Hepa-loges N; Hepa-Merz Sil; Hepar-Pasc; Heparano N; Heparsyx N; Hepatorell; Hepatos; Heplant, Legalon; Legalon SIL, Logomed Leber-Kapseln; Mariendistel Curarina; Phytohepar; Poikicholan; Probiophyt V, Silibene, Silicur, Silimarit, Silmar; Sulfolitruw H., Vit-o-Mar; Ital: Eparsil, Legalon, Locasil; Marsil; Silepar; Silimarin, Silirex, Silliver; Silmar; Trissil, S.Afr.: Legalon, Spain: Legalon; Silarine; Silimazu; Switz.: Legalon; Legalon SIL. |
| Ascorbic acid Etc. | |

*Multi-ingredient: numerous preparations

TABLE 10

| Sheep | Lipid peroxidation of sheep sera in μM MDA per ml −Chlamydia | +Chlamydia |
|---|---|---|
| Pre-vaccinated | | |
| No. 1 | 44 | 39 (89%) |
| No. 2 | 59 | 67 (114%) |
| Post-vaccinated | | |
| No. 8 | 67 | 85 (127%) |
| No. 5 | 54 | 46 (85%) |
| Post-abortion (wild type) | | |
| A | 48 | 102 (212%) |
| B | 63 | 118 (187%) |

TABLE 11

| $Me^{7-}$-binding agent, 10 μM of each | Lipid oxidising activity of anti-Chlamydia abzymes in, μM MDA/ml* | Result | Potential clinical use of agent for inhibition of anti-Chlamydia abzymes |
|---|---|---|---|
| Control | 24.3 | | |
| $NaN_1$ | 0 | Positive | Highly toxic, no use |
| KCN | 0 | Positive | Highly toxic, no use |
| Tetracycline | 18.3 | Negative | No use |
| DTPA | 45.2 | Negative | No use |
| Picolinic acid | 0 | Positive | Prooxidant, no use |

TABLE 11-continued

| $Me^{7-}$-binding agent, 10 µM of each | Lipid oxidising activity of anti-Chlamydia abzymes in, µM MDA/ml* | Result | Potential clinical use of agent for inhibition of anti-Chlamydia abzymes |
|---|---|---|---|
| $Cu^{2+}$-chelators | | | |
| DDC | 0 | Positive | Possible use ("Imutiol") |
| Acetylsalicylic acid | 6.2 | Positive | Possible use ("Aspirin") |
| Penicillamine | 0 | Positive | Possible use ("Penicillamine") |

*Each number is a mean of duplicate/triplicate measurement, and calculated as a difference between the level of MDA accumulation in the tested serum before and after the addition of 0.5 of immunisation dose of ovine Chlamydia vaccine ('Intervet').

TABLE 12

| Inhibitor | Mechanism of action | In-vitro Inhibition (+ = inhibition) (− = no inhibition) |
|---|---|---|
| Tetracycline | Fe2+ inhibition | − |
| DDC | Free and bound Cu2+ inhibition | + |
| Aspirin (acetylsalicylic acid) | Free and bound Cu2+ inhibition | + |
| Penicillamine | Free and bound Cu2+ inhibition | + |
| CN— | Free and bound Metal inhibition | + |
| N3 | Free and bound Metal inhibition | + |
| DTPA | Free metal inhibition only | − |
| Picolinic acid | Free and bound Metal inhibition | + |

TABLE 13

| | Level of activity of anti-Chlamydia abzymes in µM MDA/ml | |
|---|---|---|
| Initial of patient with CHD | Before taking aspirin | 7 days after starting to take 250 mg of aspirin daily |
| S | 45 | 0 |
| A | 100 | 20 |
| Y | 45 | 0 |

TABLE 14

| | Level of activity of anti-Chlamydia abzymes in µM MDA/ml | | |
|---|---|---|---|
| Initial of patient | Aspirin intake 250 mg daily | After stopping taking aspirin for 7 days | 7 days after re-starting to take 250 mg aspirin daily |
| F | 10 | 65 | 20 |

TABLE 15

| | Anti-Chlamydia abzyme activity, in µM MDA/ml | | |
|---|---|---|---|
| Patient | before treatment | 15 days after the start of the treatment | 30 days after the start of the treatmnet |
| 1. | 30 | 6.7 | 3.3 |
| 2. | 90 | 6.7 | — |
| 3. | 80 | 0 | 0 |
| 4. | 40 | 60 | 37 |
| 5. | 50 | 0 | 0 |
| 6. | 15 | 8.3 | 28 |
| 7. | 10 | 6.7 | 3.3 |
| 8. | 35 | 33 | 10 |
| 9. | 85 | 75 | 78 |
| 10. | 30 | 0 | 0 |
| 11. | 40 | — | — |
| | 45.9 | 19.6 | 17.7 |

TABLE 16

| | Anti-Chlamydia abzyme activity, in µM MDA/ml | |
|---|---|---|
| Patient | before treatment | 15 days after the start of the treatment |
| 12 | 100 | 43 |
| 13 | 93 | 27 |
| 14 | 33 | 0 |
| 15 | 30 | 0 |
| 16 | 153 | 0 |
| 17 | 15 | 0 |
| 18 | 25 | 3.3 |
| 19 | 15 | 0 |
| | 58.0 | 9.16 |

TABLE 17

| | Clinical condition | |
|---|---|---|
| Patient | Before treatment | After 15 days of treatment |
| 2 | Unstable angina; ECG exercise test was inapplicable | Stable condition; ECG exercise test demonstrated a significant tolerance; angina attacks were not recorded for this period; return to his job in full capacity |
| 5 | Classified as angina class III; 10 tablets of nitroglycerine daily | Based on the improvement of ECG exercise test, patient condition was reclassified as angina class II; reduction in the frequency and severity of angina attacks; 5 tablets of nitroglycerine daily; |

TABLE 20

| | Anti-Chlamydia IgG, ELISA** Day of the infection | | Anti-Chlamydia abzymes, in µM MDA/ml** Day of the infection | |
|---|---|---|---|---|
| Rabbit | 0 | 14 | 0 | 14 |
| 1 | 0 | 1:1,600 | 0 | 71 |
| 2 | 0 | 1:3,200 | — | 203 |

TABLE 20-continued

| Rabbit | Anti-Chlamydia IgG, ELISA** Day of the infection 0 | 14 | Anti-Chlamydia abzymes, in μM MDA/ml** Day of the infection 0 | 14 |
|---|---|---|---|---|
| 3 | 0 | 1:800 | 0 | 131 |
| Control | 0 | 0 | 0 | 0 |

TABLE 21

| | Anti-Chlamydia IgG, ELISA** Day of the infection | | | | Anti-Chlamydia abzymes, in μM MDA/ml** Day of the infection | | | |
|---|---|---|---|---|---|---|---|---|
| | | | 22 | | | | 22 | |
| Rabbit | 0 | 14 | | § + vaccine | 0 | 14 | | § + vaccine |
| 1 | 0 | 1:1,600 | 1:1,600 | — | 0 | 71 | 165 | — |
| 2 | 0 | 1:3,200 | 1:3,200 | — | — | 203 | 180 | — |
| 3 | 0 | 1:800 | — | 1:1,600 | 0 | 131 | — | 64 |
| Control | 0 | 0 | — | — | 0 | 0 | — | — |

TABLE 22

| Patients in Therapy Group A | Anti-Chlamydia abzyme activity, in μM MDA/ml before treatment | 15 days after the start of treatment | 30 days after the start of treatment | 45 days after the start of treatment | 60 days after the start of treatment |
|---|---|---|---|---|---|
| TGA1 | 30 | 6.7 | 3.3 | 0 | 0 |
| TGA2 | 90 | 6.7 | 78** | 17 | 3.3 |
| TGA3 | 80 | 0 | 0 | 0 | 6.7 |
| TGA4 | 40 | 60* | 37* | 0 | 0 |
| TGA5 | 50 | 0 | 0 | 20* | 0 |
| TGA6 | 15 | 8.3 | 28** | 43* | 6.7 |
| TGA7 | 28 | 6.7 | 3.3 | 3.3 | 0 |
| TGA8 | 35 | 33 | 10 | 3.3 | 0.5 |
| TGA9 | 85 | 75* | 78* | 0 | 0 |
| TGA10 | 30 | 0 | 0 | 5.0 | 0 |
| TGA11 | 40 | 52* | 10 | 0 | 0 |
| | 47.5 | 22.5 | 22.5 | 7.4 | 1.6 |

TABLE 23

| Patients in Therapy Group B | Anti-Chlamydia abzyme activity, in μM MDA/ml before treatment | 15 days after the start of treatment | 30 days after the start of treatment | 45 days after the start of treatment | 60 days after the start of treatment |
|---|---|---|---|---|---|
| TGB1 | 100 | 43 | 10 | 0 | — |
| TGB2 | 93 | 27 | 30 | 0 | 10 |
| TGB3 | 33 | 0 | 0 | 0 | 0 |
| TGB4 | 30 | 0 | 6.7 | 0 | 3.3 |
| TGB5 | 153 | 0 | 0 | 0 | 3.3 |
| TGB6 | 15 | 0 | 0 | 3.3 | 0 |
| TGB7 | 25 | 3.3 | 0 | 80** | 0 |
| TGB8 | 15 | 0 | 3.3 | 10 | 0 |
| | 58.0 | 9.16 | 6.25 | 11.6 | 2.4 |

TABLE 24

| Patients in Therapy Group C | Anti-Chlamydia abzyme activity, in μM MDA/ml before treatment | 15 days after the start of treatment | 30 days after the start of treatment | 45 days after the start of treatment |
|---|---|---|---|---|
| TGC1 | 15 | 28* | 23* | 23* |
| TGC2 | 23 | 0 | 0 | 0 |
| TGC3 | 25 | 17 | 0 | 13 |
| TGC4 | 60 | 0 | 0 | 0 |
| TGC5 | 45 | 1.7 | 0 | 0 |
| TGC6 | 43 | 18 | 0 | 0 |
| TGC7 | 140 | 53 | 20 | 20 |
| TGC8 | 130 | 57 | 17 | 3.3 |
| TGC9 | 18 | 0 | 0 | 13 |
| | 55.6 | 19.4 | 6.67 | 8.10 |

TABLE 25

| Patients in Therapy Group D | Anti-Chlamydia abzyme activity, in μM MDA/ml before treatment | 60 days after the start of treatment |
|---|---|---|
| TGD1 | 103 | 63 |
| TGD2 | 253 | 103 |
| | 178 | 83.2 |

TABLE 26

| Patient Control Group (PCG) | Anti-Chlamydia abzyme activity, in μM MDA/ml At Day 1 | At Day 60 |
|---|---|---|
| PCG1 | 43 | 43 |
| PCG2 | 93 | 70 |
| PCG3 | 60 | 53 |
| PCG4 | 17 | 25 |
| PCG5 | 70 | 55 |
| PCG6 | 25 | 23 |
| PCG7 | 20 | 34 |
| PCG8 | 70 | 68 |
| PCG9 | 20 | 20 |
| PCG10 | 30 | 27 |
| PCG11 | 20 | 45 |
| PCG12 | 170 | 150 |

TABLE 26-continued

| Patient Control Group (PCG) | Anti-Chlamydia abzyme activity, in μM MDA/ml | |
|---|---|---|
| | At Day 1 | At Day 60 |
| PCG13 | 70 | 103 |
| PCG14 | 45 | 57 |
| PCG15 | 50 | 55 |
| PCG16 | 53 | 71 |
| PCG17 | 18 | 45 |
| PCG18 | 15 | 34 |
| PCG19 | 45 | 67 |
| PCG20 | 60 | 61 |
| | 50.0 ± 7.08 | 55.3 ± 6.18 |

-continued

| Therapy Group/Patient | Score by modified Rose-Blackburn Questionnaire | |
|---|---|---|
| | Before treatment | 60 days after start of the treatment |
| TGA7 | 25 | 15 |
| TGA8 | 16 | 15 |
| TGA9 | 10 | 8 |
| TGA10 | 15 | 11 |
| TGA11 | 25 | 17 |
| | 19.4 ± 1.79 | 14.4 ± 1.14 |
| Therapy Group B | | |
| TGB1 | 21 | 19 |
| TGB2 | 17 | 14 |

TABLE 27

| Parameter | | Azithromycin Therapy Group A | Azithromycin + antioxidants Therapy Group C | Azithromycin + aspirin Therapy Group B | PCG | Norm |
|---|---|---|---|---|---|---|
| Anti-Chlamydia abzymes activity, in μM/MDA/ml | Before treatment | 47.5 ± 8.96 | 55.0 ± 16.2 | 58.0 ± 20.4 | 50.0 ± 7.08 | 6.36 ± 1.14 |
| | 60 days after treatment | 1.6 ± 0.89 $p < 0.001$* | 8.1 ± 3.60 $p < 0.05$* | 2.4 ± 1.37 $p < 0.05$* | 55.3 ± 6.18 $p > 0.05$ | |
| Anti-Chlamydia $IgG^3$, $(titers)^{-1}$ | Before treatment | 43.6 | 48.5 | 52.0 | — | 0 |
| | 60 days after treatment | 0 $p < 0.001$* | 0 $p < 0.001$* | 0 $p < 0.001$* | — | 0 |
| Clinical Status modified Rose G., Blackburn H. Questionnaire | Before treatment | 19.4 ± 1.79 | 18.6 ± 0.81 | 20.4 ± 1.79 | 19.8 ± 1.43 | 0 |
| | 60 days after treatment | 14.4 ± 1.14 $p < 0.05$* | 15.4 ± 1.75 $p > 0.05$ | 15.0 ± 1.17 $p < 0.01$* | 21.5 ± 1.19 | |
| Coagulation Silica Clotting Time**, in sec | Before treatment | | 151 ± 18.8 | | | 200–250 |
| | 60 days after treatment | | 222 ± 18.4 $p < 0.05$* | | | |

| Therapy Group/Patient | Score by modified Rose-Blackburn Questionnaire | |
|---|---|---|
| | Before treatment | 60 days after start of the treatment |
| Therapy Group A | | |
| TGA1 | 25 | 17 |
| TGA2 | 22 | 19 |
| TGA3 | 12 | 10 |
| TGA4 | 19 | 13 |
| TGA5 | 23 | 16 |
| TGA6 | 21 | 18 |

-continued

| Therapy Group/Patient | Score by modified Rose-Blackburn Questionnaire | |
|---|---|---|
| | Before treatment | 60 days after start of the treatment |
| TGB3 | 23 | 14 |
| TGB4 | 24 | 12 |
| TGB5 | 19 | 19 |
| TGB6 | 16 | — |
| TGB7 | 24 | 13 |
| TGB8 | 19 | 14 |
| | 20.4 ± 1.24 | 15.0 ± 1.17 |

-continued

| Therapy Group/Patient | Score by modified Rose-Blackburn Questionnaire Before treatment | 60 days after start of the treatment |
|---|---|---|
| Therapy Group C | | |
| TGC1 | 15 | 9 |
| TGC2 | 21 | 21 |
| TGC3 | 18 | 13 |
| TGC4 | 16 | 16 |
| TGC5 | 19 | 9 |
| TGC6 | 21 | 21 |
| TGC7 | 17 | 17 |
| TGC8 | 20 | 13 |
| TGC9 | 20 | 20 |
| | 18.6 ± 0.81 | 15.4 ± 1.75 |

TABLE 29

| Patient code | Abzyme activity Day 0 | Abzyme activity Day 60 | Rose Blackthorn Score Day 0 | Rose Blackthorn Score Day 60 |
|---|---|---|---|---|
| TGA2 | 90 | 3.3 | 22 | 19 |
| TGA3 | 80 | 6.7 | 12 | 10 |
| TGA4 | 40 | 0 | 19 | 13 |
| TGA6 | 15 | 6.7 | 21 | 18 |
| TGB3 | 15 | 0 | 23 | 14 |
| TGC5 | 45 | 0 | 19 | 9 |
| TGC7 | 140 | 20 | 17 | 17 |

TABLE 30

| Compound and its concentration | Lipid oxidising activity of anti-Chlamydia abzymes in, μM MDA/ml* | Comments |
|---|---|---|
| Control | 61 | Antioxidant properties are comparable with or stronger than α-Tocopherol |
| Azithromycin** Suspension in water | | |
| 20 μM | 0 | |
| 10 μM | 0 | |
| 2 μM | 0 | |
| 1 μM | 19 | |
| Suspension in DMSO | | |
| 5 μM | 0 | |
| 1 μM | 7 | |
| α-Tocopherol in DMSO | | |
| 10 μM | 0 | |
| 1 μM | 15 | |

| DRUGS | Anti-Abzyme accivity, in μM MDA/ml |
|---|---|
| Control | 21.7 |
| Beta Blocker | |
| 1. Propranolol Hydrochloride OBSIDAN | |
| 175 μM | 21.3 |
| 35 μM | 18.3 |
| Nitrates | |
| 1. Glyceryl Trinitrate PERLINGANIT | |
| 220 μM | 0 |
| 44 μM | 0 |
| 22 μM | 0 |
| 4.4 μM | 0 |
| 2. Isosorbide Dinitrate ISOKET | |
| 211 μM | 0 |
| 42 μM | 0 |
| Magnesium | |
| 1. Magnesium Sulfate | |
| 101 μM | 0 |
| 51 μM | 0 |
| 40 μM | 16 |
| 20 μM | 26 |
| 1. Heparin | |
| Heparin | |
| 0.1 mg/ml | 19.7 |
| 2. Nadroparin Calcium FRAXIPARINE | |
| 65 UI | 12.8 |
| 5 UI | 20.5 |
| Calcium - Channel Blocker | |
| Verapamil Hydrochloride ISOPTIN | |
| 51 μM | 3 |
| 10.2 μM | 24.0 |
| 5.1 μM | 21.5 |
| Corticosteroids | |
| 1. Dexamethasone | |
| 25 μM | 24.5 |
| 12.5 μM | 20.1 |
| Antibiotics | |
| 1. Lincomycin Hydrochloride | |
| 13 μM | 30.3 |
| 6.5 μM | 28.5 |

TABLE 32

| | | Abbreviation for clotting time measurements | Means of results from patient therapy groups A, B, C and D groups | Abbreviation for clotting time measurements | Not treated Patient Control Group (PCG) | Our Clinically Healthy Control Group |
|---|---|---|---|---|---|---|
| Coagulation* | Before treatment | APTT | 22.4 ± 0.89 | | | |
| | | PT | 13.5 ± 0.94 | | | |
| | | SCT | 151 ± 15.0 | APTT | 25.2 ± 1.37 | 49.1 ± 7.00 |
| | | KCT | 51.2 ± 4.59 | | | |
| | 60 days after treatment | APTT | 46.9 ± 6.45<br>p < 0.005* | PT | 17.3 ± 4.05 | 23.7 ± 4.01 |
| | | PT | 25.3 ± 4.05<br>p < 0.05* | SCT | 137 ± 11.5 | 248 ± 10.0 |
| | | SCT | 235 ± 17.9<br>p < 0.005* | KCT | 50.3 ± 2.16 | 133 ± 23.7 |
| | | KCT | 126 ± 34.2<br>p > 0.05 | | | |

TABLE 18

| | | | | MYOCARDIAL INFARCTION | |
|---|---|---|---|---|---|
| CONTROL | SILENT ISCHAEMIA | STABLE ANGINA | UNSTABLE ANGINA | Acute Phase 1st–3rd Day | $14^{th}$ Day |
| 6.36 ± 1.14<br>(n = 67)<br>11/67 = 16% | 68.8 ± 16.7<br>(n = 15)<br>14/15 = 93%<br>$P_{control} < 0.001$ | 37.1 ± 2.23<br>(n = 193)<br>130/193 = 67%<br>$P_{control} < 0.001$ | 101 ± 18.1<br>(n = 13)<br>12/13 = 92%<br>$P_{control} < 0.001$<br>$P_{stable\ angina} < 0.001$ | 14.4 ± 2.60<br>(n = 25)<br>12/25 = 48%<br>$P_{control} < 0.01$<br>$P_{unstable\ angina} < 0.001$ | 80.6 ± 21.4<br>(n = 14)<br>12/14 = 86%<br>$P_{acute\ phase} < 0.01$ |

TABLE 19

| ISCHAEMIC HEART DISEASE (total): 168/235 = 71% | | | | | | | |
|---|---|---|---|---|---|---|---|
| STABLE ANGINA | | | | | | UNSTABLE ANGINA | |
| I | | II | | III | | IV | |
| | + aspirin | | + aspirin | | + aspirin | | + aspirin |
| 15 | 0 | 45 | 30 | 45 | 20 | 70 | 180 |
| 75 | 5 | 0 | 5 | 40 | 0 | 90 | 130 |
| 15 | 45 | 70 | 10 | 10 | 45 | 30 | 70 |
| 15 | 0 | 50 | 10 | 45 | 0 | 250 | 0 |
| | 10 | 20 | 0 | 60 | 5 | 140 | 37 |
| | 0 | 0 | 5 | 90 | 35 | 130 | 90 |
| | | 8 | 25 | 25 | 0 | | 100 |
| | | 0 | 0 | 30 | 15 | | |
| | | 53 | 5 | 153 | 30 | | |
| | | 18 | 22.5 | 15 | 105 | | |
| | | 17 | 0 | 93.3 | | | |
| | | 43 | 5 | | | | |
| | | 10 | 3.3 | | | | |
| | | 50 | 0 | | | | |
| | | 32.5 | 16.7 | | | | |
| | | 100 | | | | | |
| | 1/6 | | 4/15 | | 6/10 | | 6/7 |
| | 17% | | 27% | | 60% | | 86% |
| 30.0 (n = 4) | 10.0 (n = 6) | 32.2 (n = 16) | 9.2 (n = 15) | 56.0 (n = 11) | 25.5 (n = 10) | 119 (n = 6) | 86.7 (n = 7) |
| 4/9 = 44% | | 12/26 = 46% | | 12/17 = 71% | | 12/13 = 92% | |

What is claimed is:

1. A method for assessing an individual for an atherosclerotic disorder comprising:

(a) testing the ability of an IgG molecule from a serum sample obtained from the individual to oxidise lipid, and (b) testing the ability of any lipid oxidising IgG molecules to bind to a *Chlamydia* cell from a species belonging to the *Chlamydia psittaci* group, wherein the presence in said sample of lipid oxidising IgG molecules which bind to a *Chlamydia* cell from a species belonging to the *Chlamydia psittaci* group is indicative that the individual has an atherosclerotic disorder.

2. The method according to claim 1 wherein lipid oxidation activity of said IgG molecule is determined by determining the production of a lipid oxidation product as a result of contacting said IgG molecule with a lipid.

3. The method according to claim 2 wherein the lipid oxidation product is malondialdehyde (MDA).

4. The method according to claim 1 comprising determining the amount in said sample of lipid oxidising IgG molecules which bind to a *Chlamydia* cell from a species belonging to the *Chlamydia psittaci* group.

5. The method according to claim 1 wherein said atherosclerotic disorder is atherosclerosis.

6. The method according to claim 1 wherein the Chlamydial cell is a *Chlamydia psittaci* cell.

7. The method according to claim 6 wherein the Chlamydial cell is an ovine *Chlamydia psittaci* cell.

8. A method for assessing an individual for an atherosclerotic disorder comprising:

(a) testing the ability of an IgG molecule from a serum sample obtained from the individual to bind to a *Chlamydia* cell from a species belonging to the *Chlamydia psittaci* group, (b) testing the ability of any IgG molecules which bind to a *Chlamydia* cell from a species belonging to the *Chlamydia psittaci* group to oxidise lipid, wherein the presence in said sample of lipid oxidising IgG molecules which bind to a *Chlamydia* cell from a species belonging to the *Chlamydia psittaci* group is indicative that the individual has an atherosclerotic disorder.

9. The method according to claim 8 wherein lipid oxidation activity of said IgG molecule is determined by determining the production of a lipid oxidation product as a result of contacting said IgG molecule with a lipid.

10. The method according to claim 9 wherein the lipid oxidation product is malondialdehyde (MDA).

11. The method according to claim 8 comprising determining the amount in said sample of lipid oxidising IgG molecules which bind to a *Chlamydia* cell from a species belonging to the *Chlamydia psittaci* group.

12. The method according to claim 8 wherein said atherosclerotic disorder is atherosclerosis.

13. The method according to claim 8 wherein the Chlamydial cell is a *Chlamydia psittaci* cell.

14. The method according to claim 13 wherein the Chlamydial cell is an ovine *Chlamydia psittaci* cell.

15. A method for assessing an individual for an atherosclerotic disorder comprising:

testing the ability of an IgG molecule from a serum sample obtained from the individual to bind to a *Chlamydia* cell from a species belonging to the *Chlamydia psittaci* group and to oxidise lipid, wherein the presence in said sample of lipid oxidising IgG molecules which bind to a *Chlamydia* cell from a species belonging to the *Chlamydia psittaci* group is indicative that the individual has an atherosclerotic disorder.

16. The method according to claim 15 wherein lipid oxidation activity of said IgG molecule is determined by determining the production of a lipid oxidation product as a result of contacting said antibody with a lipid.

17. The method according to claim 16 wherein the lipid oxidation product is malondialdehyde (MDA).

18. The method according to claim 15 comprising determining the amount of said antibody molecule in said sample.

19. The method according to claim 15 wherein said atherosclerotic disorder is atherosclerosis.

20. The method according to claim 15 wherein the Chlamydial cell is a *Chlamydia psittaci* cell.

21. The method according to claim 20 wherein the Chlamydial cell is an ovine *Chlamydia psittaci* cell.

* * * * *